United States Patent [19]

Lawman et al.

[11] Patent Number: 5,256,560
[45] Date of Patent: Oct. 26, 1993

[54] PRIMITIVE CELL COLONY STIMULATING FACTORS AND LYMPHOHEMATOPOIETIC PROGENITOR CELLS

[75] Inventors: Michael J. P. Lawman, Gainsville, Fla.; Helle B. Ohmann; Samuel K. Attah-Poku; Janette Heise-Qualtiere, all of Saskatchewan, Canada

[73] Assignee: University of Saskatchewan, Saskatoon, Canada

[21] Appl. No.: 677,617

[22] Filed: Mar. 27, 1991

Related U.S. Application Data

[63] Continuation of Ser. No. 255,088, Oct. 7, 1988, abandoned.

[51] Int. Cl.$^5$ .................... C12N 5/00; C12N 5/02
[52] U.S. Cl. ...................... 435/240.2; 435/240.21; 435/240.25
[58] Field of Search ............ 435/240.1, 240.2, 240.25, 435/240.3, 240.21, 240.25; 514/2; 424/93 U, 577

[56] References Cited

U.S. PATENT DOCUMENTS

| | | |
|---|---|---|
| 4,438,032 | 3/1984 | Golde et al. |
| 4,710,457 | 12/1987 | Dupont et al. |
| 4,714,680 | 12/1987 | Civin ............................... 435/240.25 |
| 4,721,096 | 1/1988 | Naughton et al. .................. 128/1 R |
| 4,808,611 | 2/1989 | Cosman .............................. 514/12 |
| 4,845,078 | 7/1989 | Masaoka ............................. 514/8 |

FOREIGN PATENT DOCUMENTS

WO90/04018 4/1990 PCT Int'l Appl.

OTHER PUBLICATIONS

Spangrude et al., Science 241:58–62 (1988).
Quesenberry et al., Blood Cells 13:137–146 (1987).
Gordon et al., British J. Hematology 60:129–136 (1985).
Köhler et al., Nature (1975) 256:495–497.
Namen, A. E., et al., "B Cell Precursor Growth-Promoting Activity: Purification and Characterization of a Growth Factor Active on Lymphocyte Precursors", *J. Experimental Medicine* (1988) 167:988–1002.
Hunt, P., et al., "A Single Bone Marrow-Derived Stromal Cell Type Supports the In Vitro Growth of Early Lymphoid and Myeloid Cells", *Cell* (1987) 48:997–1007.
Sleff, *J. Clin. Invest.* (1987) 79:1549–1567.
Mitjavila et al., *J. Cellular Phys.* (1989) 138:617–623.
Andrews et al., *J. Exp. Med.* (1989) 169:1721–1731.
Johnston, Jr., *New Engl. J. Med.* (1988) 318(12):747–752.
Nienhuis, *New Engl. J. Med.* (1988) 318(14):916–918.
Friend, *USA Today Newspaper* (Apr. 7, 1988) "Protein Gives Chemotherapy Patients Relief," Life Sciences Section, p. 10D.

*Primary Examiner*—Jasemine C. Chambers
*Attorney, Agent, or Firm*—Morrison & Foerster

[57] ABSTRACT

The invention derives from the discovery of cells, non-adherent (NA) cells, which have properties indicating that they may be pluripotent lymphohematopoietic progenitor cells. These cells, and the stromal cells derived from bone marrow cultures, produce factors which stimulate the growth of primitive cell colonies, as reflected in their stimulation of the growth of colonies of NA cells. These primitive cell colony stimulating factors (PC-CSFs) may be useful in the treatment of disorders which can be alleviated by the proliferation of desired cells. In addition, the NA cells and/or PC-CSF(s) may provide an alternative and/or supplementary method to bone marrow transplantation to alleviate hematopoietic disorders.

8 Claims, 9 Drawing Sheets

| TREATMENT | UNDILUTE | 2 | 4 | 8 | 16 | 32 | 64 | 128 | 256 |
|---|---|---|---|---|---|---|---|---|---|
| NORMAL MEDIUM[1] | - |  | - | - | - | - | - | - | - |
| MEDIUM FROM PBL[2] CULTURES | - |  | - | - | - | - | - | - | - |
| BONE MARROW SUPNT[3] | - |  | - | - | - | - | - | - | - |
| PC-CSF SUPNT | +++[5] | +++ | + | + | ± | - | - | - | - |

1. RPMI-1640 + 10% FBS

2. MEDIUM (FILTERED THROUGH 0.22 MICRON FILTER) HARVESTED FROM 24 HOUR CULTURES OF BOVINE PERIPHERAL BLOOD LEUKOCYTES.

3. MEDIUM (FILTERED THROUGH 0.22 MICRON FILTER) HARVESTED FROM 6 HOUR WHOLE BONEMARROW CULTURE.

5. COLONIES WERE GROWN FOR 14 DAYS BEFORE ENDING EXPERIMENT.

FIG. 5

PRIMITIVE CELL COLONY STIMULATING FACTORS AND LYMPHOHEMATOPOIETIC PROGENITOR CELLS

This application is a continuation of application Ser. No. 255,088, filed Oct. 7, 1988, now abandoned.

TECHNICAL FIELD

The present invention is directed to cell populations useful in bone marrow transplantation and to cytokines involved in the proliferation of bone marrow cells.

BACKGROUND OF THE INVENTION

In both veterinary medicine and human medicine, the ability to initiate and regulate hematopoiesis is of great importance. A variety of diseases and immune disorders, as well as malignancies, appear to be related to disruptions within the hematopoietic system. Many of these disorders could be alleviated and/or cured by repopulating the hematopoietic system with progenitor cells which, when triggered to differentiate, would overcome the individual's deficiency. In humans, a current replacement therapy is bone marrow transplantation. This form of therapy, however, is both painful for both donor and recipient, and is of severe danger to the recipient, particularly when the grafts are allogeneic. Even though prior to bone marrow transplantation, the donor and recipient are matched with respect to HLA types, approximately half of the allogeneic bone marrow transplant recipients develop Graft Versus Host Disease (GVHD). Current therapy for GVHD is imperfect, and the disease can be disfiguring and/or lethal. Thus, risk of GVHD restricts the use of bone marrow transplantation to patients with otherwise fatal diseases, such as severe immunodeficiency disorders, severe aplastic anemia, and malignancies.

The potential benefits of bone marrow transplantation have stimulated research on the cause and prevention of GVHD. In animal studies it has been shown that GVHD is caused by donor T lymphocytes. Removal of T lymphocytes from donor marrow inocula ("grafts") attenuated the subsequent development of GVHD in mice, dogs and monkeys. Trials in humans, in which bone marrow has been depleted of T lymphocytes by a variety of methods, however, has not prevented or cured GVHD in bone marrow recipients.

A potential alternative form of therapy for hematopoietic disorders is treatment of the individual with any one or combination of colony stimulating factors. The process of blood cell formation, by which a small number of self-renewing stem cells give rise to lineage committed progenitor cells that subsequently proliferate and differentiate to produce the circulating mature blood cells, is sustained throughout life by a group of glycoprotein hormonal growth factors. These hormones are known collectively as the colony stimulating factors (CSFs).

DESCRIPTION OF THE RELATED ART

The term colony stimulating factor was derived from the in vitro observation that the CSFs stimulate progenitor cells of different hematopoietic cell lineages to form discrete colonies of recognizable maturing cells. The different factors have been operationally defined by prefixes denoting the major type of colony produced. The genes for five murine and human CSFs have been cloned, and recombinant forms of the proteins produced and purified. These factors include multi-potential CSF (multi-CSF), granulocyte-macrophage CSF (GM-CSF), granulocyte CSF (GCSF), macrophage CSF(MCSF), and erythropoietin. A review of the characteristics of these factors, which also describes the major target cells, is presented in Sieff (1987) J. Clin. Invest. 79: 1549.

DISCLOSURE OF THE INVENTION

It is an object of the present invention to provide alternative and/or adjunct methods to bone marrow transplant as a therapy for hematopoietic disorders.

Non-adherent (NA) cell lines have been generated from bone marrow stromal cultures isolated from various species. The original NA cell line was generated from cultures of bovine stromal cell monolayers. Using culture supernatants from the parent bovine bone marrow cell line, morphologically similar NA cell lines were obtained from other bovine bone marrow stromal cultures and from bovine bone marrow. NA cell lines have also been induced by the cell culture supernatant factor(s) in cultures of stromal cells derived from other species, including human, porcine, murine, and avian bone marrows. Surprisingly, the NA cells, based upon morphological, functional, and phenotypic analyses, appear to be of a very primitive nature and may in fact be pluripotent lymphohematopoietic progenitor cells. These cells also appear to home to hematopoietic tissue, and may have use in treating hematopoietic disorders.

Protein factors, primitive cell colony stimulating factors (PC-CSFs), have been identified in and isolated from the supernatant of NA cell cultures and stromal cell cultures derived from bone marrow. These PC-CSFs stimulate the proliferation of cells, particularly of NA cells. Thus, these factors may have use in treating disorders which can be alleviated by the proliferation of cells, including, for example, wound healing, and neuronal disorders. In particular, they may have use in the treatment of hematopoietic disorders by causing a proliferation of lymphohematopoietic stem cells which either exist in the individual being treated, or which were injected into the individual as part of a treatment program for a hematopoietic disorder.

Accordingly, one embodiment of the invention is purified primitive cell colony stimulating factor (PC-CSF).

Another embodiment of the invention is a recombinant vector encoding PC-CSF, and a cell transformed with this vector.

Yet another embodiment of the invention is purified PC-CSF-alpha.

Still another embodiment of the invention is purified PC-CSF-beta.

Another embodiment of the invention is a suspension of cells comprised of pluripotent lymphohematopoietic progenitor cells (NA cells) substantially free of mature lymphoid and myeloid cells.

Still another embodiment of the invention is a suspension of NA cells derived from a human, wherein said cells are not immunologically reactive with a monoclonal antibody directed against My10 antigen, said monoclonal antibody being produced by hybridoma cell line ATCC Accession No. HB-8483.

Another embodiment of the invention is a hybridoma which produces a monoclonal antibody which is immunologically reactive with a NA cell derived from bone marrow, and the monoclonal antibody produced by the hybridoma.

Still another embodiment of the invention is a method of producing a population of cells containing NA cells comprising: providing a cell suspension comprising NA cells; growing the cell suspension in a culture medium comprised of PC-CSF and other components essential to cell growth under conditions which promote cell growth; isolating and recovering a population of NA (NA) cells from the cell culture; and growing the isolated cells in a culture medium comprised of PC-CSF and other components essential to cell growth under conditions which promote cell growth.

Yet another embodiment of the invention is a method of producing a population of cells containing pluripotent lymphohematopoietic progenitor cells comprising: providing a cell suspension from an individual's hematopoietic tissue; contacting the cell suspension with a monoclonal antibody to NA cells, said antibody recognizing an antigen on the NA cells but not recognizing an antigen on more mature lymphoid and myeloid cells; and separating and recovering from said cell suspension the cells bound by said antibody.

Another embodiment of the invention is a method of treating an individual for a disorder of the hematopoietic system comprising: providing a suspension of NA cells in a pharmaceutically acceptable medium; injecting the individual with a dose of NA cells in an amount sufficient to overcome the hematopoietic disorder. The individual may be further treated by injecting a solution of PC-CSF in a pharmaceutically acceptable excipient, in a dose sufficient to stimulate the proliferation of NA cells in the individual.

Still another embodiment of the invention is a method of treating an individual for a disorder which is alleviated by cell proliferation comprising: providing a solution of PC-CSF in a pharmaceutically acceptable excipient; and applying to the individual a pharmacologically effective dose of PC-CSF which alleviates the symptoms of the disorder by causing proliferation of the desired cells. The individual may be treated for a hematopoietic disorder, wherein the applying is of a dose of PC-CSF which alleviates the hematopoietic disorder. The individual may be treated for a wound, wherein the applying is of a dose of PC-CSF which stimulates wound healing. The individual may be treated for a disorder of neuronal origin, wherein the applying is of a dose of PC-CSF which stimulates neuronal regeneration.

BRIEF DESCRIPTION OF THE DRAWINGS

FIGS. 1A and 1B are without and with IL-2, respectively.

FIGS. 2A and 2B are without and with IL-2, respectively.

FIGS. 3A and 3B are without and with IL-2, respectively.

FIG. 5 is a chart showing the effect of PC-CSF containing supernatant upon the growth of NA cells.

MODES FOR CARING OUT THE INVENTION

I. Definitions

Figure 1A:
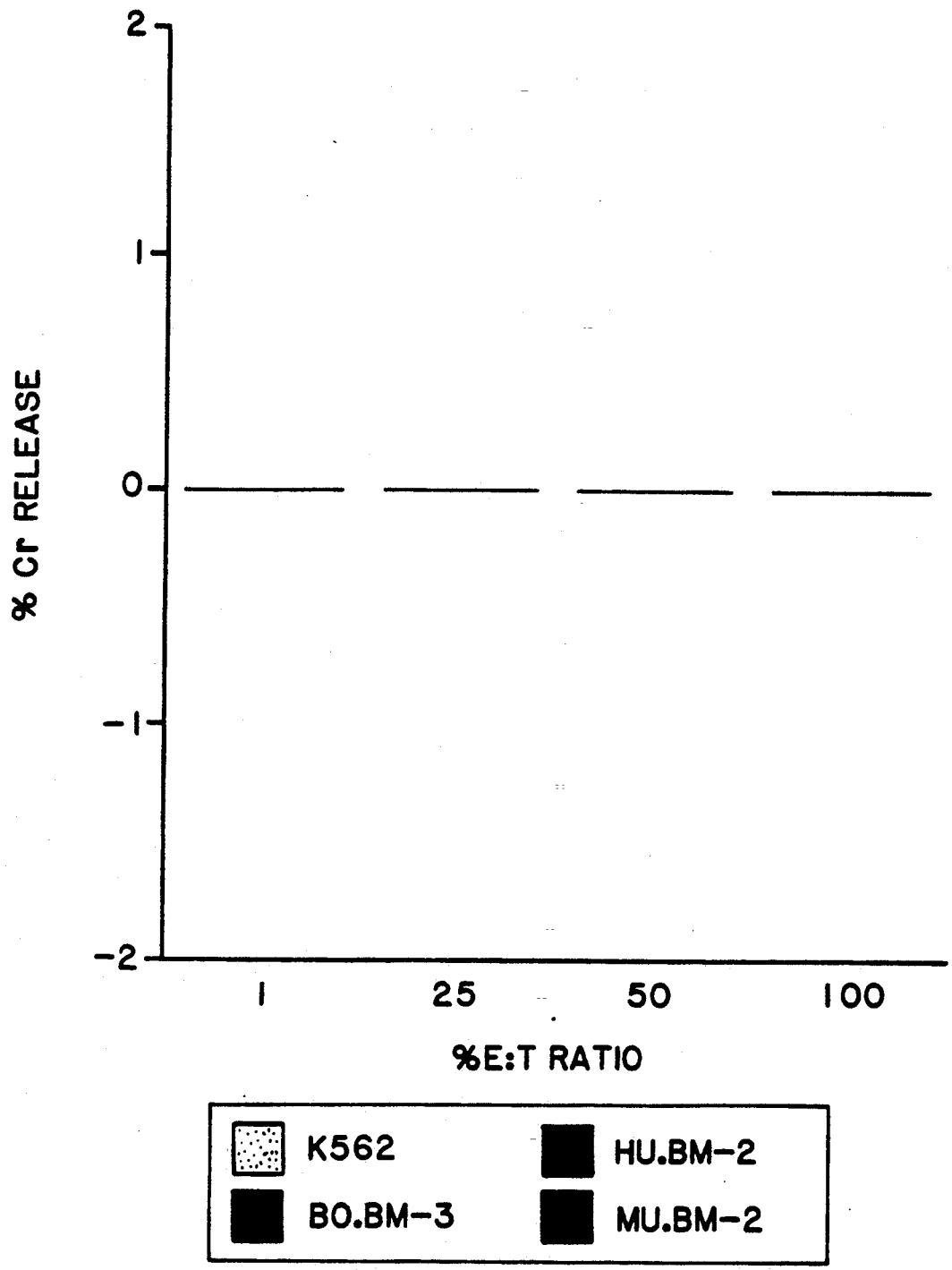
FIGS. 1A, 1B are graphs which shows the cytotoxic effect of bovine NK cells on bovine NA cells.

An "individual", as used herein, refers to vertebrates, particularly members of the mammalian species or avian species, and includes but is not limited to domestic animals, sports animals, primates, and humans.

As used herein, "Primitive cell colony stimulating factor" ("PC-CSF") means the factor(s) derived from individuals, which cause long term proliferation of adherent and/or non-adherent cells from bone marrow stromal cultures. The individuals from which the PC-CSF(s) are derived are vertebrates, are preferably mammals, and are more preferably of the bovine, murine, porcine, or human species. The term "PC-CSF" is meant to include analogs and fragments of the factors which exhibit the biological activity of stimulating the appearance and proliferation of non-adherent bone marrow cells in bone marrow stromal cultures and/or whole bone marrow cultures. This biological activity may be detected by, for example, the assays described in Examples 13 and 16, infra.

"Purified PC-CSF" refers to a PC-CSF which is essentially free of cellular components and other soluble products with which PC-CSF is naturally associated. Techniques for purifying polypeptides such as PC-CSF are known in the art, and are discussed infra. As used herein, "essentially free" means at least about 50% free of the cellular components and soluble products, preferably at least about 70% free of the components and soluble products, and even more preferably at least about 90% free of the components and soluble products.

As used herein, unless otherwise specifically defined, the term "cultures" means bone marrow cell cultures which produce PC-CSF, and which may produce other factors which are cytokines of an immunoregulatory nature. "Cultures" may be comprised of adherent cells and/or non-adherent cells derived from bone marrow. The terms cell "culture" and cell "line" are used interchangeably. Cell cultures or cell lines refers to various embodiments including but not limited to individual cells, harvested cells, and cultures containing cells so long as these are derived from the cell line referred to. By "derived" is meant progeny or issue. It is further known in the art that spontaneous or induced changes can take place in karyotype during storage or transfer. Therefore, cells derived from the cell line referred to may not be precisely identical to the ancestral cells or cultures, and a cell culture referred to includes such variants.

"Pluripotent lymphohematopoietic progenitor cells" are cells which exhibit the following characteristics. They are derived from bone marrow stromal cultures, and particularly from non-adherent cells which are induced to proliferate by PC-CSF in the culture supernatant. Morphologically, they resemble cells of a monocyte-macrophage lineage. Phenotypically, the cells lack T cell specific antigens, MHC class II antigens, macrophage/monocyte markers, and B cell markers. Treatment of the cells with IL-2 does not facilitate the cells into becoming lymphokine activated killer cells. Treatment with IFN-gamma, IFN-alpha, and TNF-alpha does not induce the induction of the production of reactive oxygen species by the cells, nor an induction of vectorial migration to C5a, a potent chemotactic peptide. Treatment of the cells with IFN-gamma, IFN-alpha, and TNF-alpha does not induce cell proliferation, nor does it induce a change in the morphology of the cells. The pluripotent lymphohematopoietic stem cells home to hematopoietic tissue, are tumorigenic, and give rise to undifferentiated colonies in a CFU-S assay. The terms "pluripotent lymphohematopoietic progenitor cells" and "non-adherent cells" are used interchangeably herein.

A "clone", as used herein, refers to the progeny of a single cell.

"Recombinant host cells", and "host cells" refers to cells of microorganisms or eukaryotic cells which can be, or have been, used as recipients for recombinant vector or other transfer DNA, and include the progeny of the original cell which has been transfected or transformed. It is understood that the progeny of a single parental cell may not necessarily be completely identical in morphology or in genomic or total DNA complement as the original parent, due to accidental or deliberate mutation. Progeny of the parental cell which are sufficiently similar to the parent to be characterized by the relevant property, such as the presence of a nucleotide sequence encoding a desired peptide, are included in the progeny intended by this definition, and are covered by the above terms.

"Transformation", as used herein, refers to the insertion of an exogenous polynucleotide into a host cell, irrespective of the method used for the insertion, for example, direct uptake, transduction, or f-mating. The exogenous polynucleotide may be maintained as a non-integrated vector, for example, a plasmid, or alternatively, may be integrated into the host genome.

The term "recombinant polynucleotide", as used herein to characterize a polynucleotide encoding PC-CSF, intends a polynucleotide of genomic, cDNA, semisynthetic, or synthetic origin which, by virtue of its origin or manipulation: (1) is not associated with all or a portion of the polynucleotide with which it is associated in nature or in the form of a library; and/or (2) is linked to a polynucleotide other than that to which it is linked in nature.

The term "polynucleotide" as used herein refers to a polymeric form of nucleotides of any length, either ribonucleotides or deoxyribonucleotides. This term refers only to the primary structure of the molecule. Thus, double- and single-stranded DNA, as well as double- and single stranded RNA are included. It also includes modified, for example by methylation and/or by capping, and unmodified forms of the polynucleotide.

A "replicon" is any genetic element, e.g., a plasmid, a chromosome, a virus, that behaves as an autonomous unit of polynucleotide replication within a cell; i.e., capable of replication under its own control.

A "vector" is a replicon in which another polynucleotide segment is attached, so as to bring about the replication and/or expression of the attached segment.

"Control sequence" refers to polynucleotide sequences which are necessary to effect the expression of coding sequences to which they are ligated. The nature of such control sequences differs depending upon the host organism; in prokaryotes, such control sequences generally include promoter, ribosomal binding site, and terminators; in eukaryotes, generally, such control sequences include promoters, terminators and, in some instances, enhancers. The term "control sequences: is intended to include, at a minimum, all components whose presence is necessary for expression, and may also include additional components whose presence is advantageous, for example, leader sequences.

"Operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences.

An "open reading frame" is a region of a polynucleotide sequence which encodes a polypeptide; this region may represent a portion of a coding sequence or a total coding sequence.

A "coding sequence" is a polynucleotide sequence which is transcribed into mRNA and/or translated into a polypeptide when placed under the control of appropriate regulatory sequences. The boundaries of the coding sequence are determined by a translation start codon at the 5'-terminus and a translation stop codon at the 3'-terminus. A coding sequence can include, but is not limited to mRNA, cDNA, and recombinant polynucleotide sequences.

"Immunologically identifiable with/as" refers to the presence of epitope(s) in the cellular antigen which are also present in the cell type in which the antigen was originally identified. Immunological identity may be determined by antibody binding and/or competition in binding; these techniques are known to those of average skill in the art, and are also illustrated infra.

As used herein, "epitope" refers to an antigenic determinant of a polypeptide; an epitope could comprise 3 amino acids in a spatial conformation which is unique to the epitope; generally, an epitope consists of at least 5 such amino acids, and more usually, consists of at least 8–10 such amino acids.

An antigen is "immunologically reactive" with an antibody when it binds to an antibody due to antibody recognition of a specific epitope contained within the polypeptide. Immunological reactivity may be determined by antibody binding, more particularly by the kinetics of antibody binding, and/or by competition in binding using as competitor(s) a known antigen containing an epitope against which the antibody is directed. The techniques for determining whether an antigen is immunologically reactive with an antibody are known in the art.

The term "polypeptide" refers to the amino acid product of a sequence encoded within a genome, and does not refer to a specific length of the product; thus, peptides, oligopeptides, and proteins are included within the definition of polypeptide. This term also does not refer to post-expression modifications of the polypeptide, for example, glycosylations, acetylations, phosphorylations, and the like.

"Treatment", as used herein, refers to prophylaxis and/or therapy.

As used herein, the term "disorder of the hematopoietic system" refers to disorders which result from the following: a change in the differentiation program involved in hematopoiesis, for example, clonal neoplasms of hematopoietic tissue (which include myeloid and lymphoid neoplasms), immune deficiency diseases, lymphopenia; genetic defects related to a mutation in a structural gene for an essential protein, for example, in humans, alpha-thalassemia, and sickle cell disease; genetic defects related to immune responsiveness, including autoimmune diseases, particularly those related to abnormal T-cell subsets, for example, in humans, connective tissue diseases such as systemic lupus erythematosus, acute GVHD, autoimmune hemolytic anemia, multiple sclerosis, myasthenia gravis, inflammatory bowel disease, and atopic eczema.

II. Description of the Invention

The practice of the present invention will employ, unless otherwise indicated, conventional techniques of cell biology, cell culture, molecular biology, microbiology, recombinant DNA, and immunology, which are within the skill of the art. Such techniques are explained fully in the literature. See, for example, Maniatis et al., Molecular Cloning: A Laboratory Manual (1982); DNA Cloning, Volumes I and II (D. N. Glover ed., 1985); Oligonucleotide Synthesis (M. J. Gait ed., 1984); Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987), and Handbook Of Experimental Immunology, Volumes I-IV (D. M. Weir and C. C. Blackwell, eds., 1986).

All patents, patent applications, and publications mentioned herein, both supra and infra, are hereby incorporated by reference.

II.A. Cell Lines

Novel cell lines which are comprised of lymphohematopoietic progenitor cells were isolated from bone marrow cultures from several species. The cells, which are also called "non-adherent" (NA) cells, exhibit the following characteristics. They are primitive in morphology. They lack certain cell surface markers which are characteristic of lymphoid and myeloid cells, and of stem cells to these lines, as shown in the Examples. Under in vitro conditions, these cells do not differentiate into cells of either the lymphoid or myeloid series, despite the presence of the following lymphokines: interleukin 2 (IL-2), gamma interferon (IFN-gamma), alpha interferon (IFN-alpha), and alpha tumor necrosis factor (TNF-alpha). However, when injected into a homologous species, the NA cells appear to home to hematopoietic tissue (for example, bone marrow) in the inoculated individuals. In addition, the cells exhibit hematopoietic potential in an assay which is known to measure the hematopoietic potential of pluripotent stem cells, i.e., the CFU-S assay. Thus, these cells appear to be multipotent progenitor cells.

Stromal cells and NA cells secrete factors which apparently induce the NA cells to replicate without undergoing differentiation. One of these factors, which appears to be secreted by the murine NA cells in culture, has an apparent molecular weight of approximately 20-25 Kd, and has been named "primitive cell colony stimulating factor alpha" (PC-CSF-alpha). Another factor appears to be a product of the murine bone marrow stromal culture, and has an apparent molecular weight of approximately 60-70 Kd; this factor has been named primitive cell colony stimulating factor beta (PC-CSF-beta).

II.B. PC-CSF

PC-CSF activity is monitorable by its effect on inducing the proliferation of NA cells. Two types of suitable assay for PC-CSF activity are described in the Examples (See Examples 15 and 16, which describe an assay comprised of NA cells and stromal cells, and a clonogenic assay, respectively). It is of interest that PC-CSF isolated from one species appears to be able to induce the proliferation of NA cells from another species.

Utilizing conventional techniques for the isolation of proteins, PC-CSF can be concentrated and substantially freed of other proteinaceous components of the NA cell conditioned medium. Techniques for protein purification are known to those of ordinary skill in the art, and include, for example, separation of the component by precipitation, separation by adsorption including, for e.g., adsorption on ion exchangers, on affinity materials, by dye ligand chromatography, and by immunoadsorbents, and separation in solution by gel filtration, for e.g., by electrophoresis, by isoelectric focusing, by isotacophoresis, by liquid phase partitioning, and by ultrafiltration. See, Scopes (1987). A method by which PC-CSF may be purified is described in the Examples.

Although PC-CSF may be isolated from conditioned media, and from hematopoietic tissue, it may also be synthesized utilizing recombinant DNA techniques. In these techniques, a recombinant sequence encoding PC-CSF is inserted into an expression vector such that the control sequences are operably linked to the recombinant PC-CSF encoding sequence. Host cells are transformed with the recombinant vectors, and, under suitable growth conditions, express recombinant PC-CSF.

The recombinant sequence encoding PC-CSF may be derived from sequences isolated by known techniques in molecular biology, for example, by the screening of cDNA or genomic libraries, or if the mRNA is in relatively high abundance, by reverse transcription of isolated mRNA encoding PC-CSF.

A probe, prepared as described below for the screening of libraries, may be used as a probe to isolate the mRNA which is translated to the desired protein. The NA cells can be lysed, and the RNA separated from the DNA. A poly(A) enriched fraction, which contains mRNA, may then be separated utilizing a column of oligo-dT or -dU. The mRNA of interest can be further purified by electrophoresis, and using the Northern technique, identified by a $^{32}$-P labeled probe. Once the mRNA has been identified, it can be excised from a preparative gel.

The sequence encoding PC-CSF can be prepared from the mRNA by reverse transcription of the mRNA, utilizing reverse transcriptases which are commercially available. The resulting cDNA is cloned, and preferably is sequenced. The recombinant cDNA is then inserted into an expression vector, such that the sequences which control expression are operably linked to the PC-CSF coding sequence.

In an alternative procedure(s), a cDNA library and/or a genomic library may be prepared from bone marrow cells, preferably from NA cells and/or stromal cells, and more preferably from NA cells. Techniques for preparing cDNA libraries are known in the art. See, for example, Maniatis et al. (1982), and DNA Cloning Vols. I and II (1985). The type of library constructed may be one which may be screened with oligonucleotide probes designed to detect the sequences encoding PC-CSF, for example, a library constructed in lambda gt10.

In order to screen the library(s), a probe is constructed which encodes or which is the complement of a sequence which encodes a fragment of PC-CSF. The probe is any length which will allow the detection of PC-CSF sequences by hybridization, is preferably about 9 to about 120 nucleotides in length, and is even more preferably about 30 to about 60 amino acids in length. The recombinant polynucleotide probe is constructed from the amino acid sequence of a polypeptide fragment of PC-CSF. Utilizing purified PC-CSF, a portion of the molecule can be sequenced. The portion sequenced will be of sufficient size to yield a probe of the desired length. Techniques for determining the amino acid sequence of fragments of a polypeptide are known by those of ordinary skill in the art. Generally, the protein of interest is specifically cleaved into small peptides to facilitate analysis. Specific cleavage can be achieved by chemical or enzymatic methods. Examples of chemical cleavage methods include treatment with Cyanogen bromide, 0-iodosobenzoate, hydroxylamine, and 2-nitro-5-thiocyanobenzoate. Examples of methods utilizing proteolytic enzymes include treatment with trypsin, clostripain, and staphylococcal protease. The amino acid composition of identified fragments may be determined, and the fragments may then be subjected to amino acid analysis by automated Edman degradation using, for example, a sequenator. Sequenators are commercially available, and sequencing may be accomplished according to the manufacturer's directions. The peptide fragments of PC-CSF are usually derived by two different methods to allow the analysis of overlapping fragments.

Based upon the observed sequence of the peptide derived from PC-CSF, recombinant polynucleotide probes can be designed which would encode the PC-CSF fragment by reverse translating the amino acid sequence into a polynucleotide sequence. These probes would take into account the preferred codon usage in the species from which the PC-CSF was isolated.

Screening of the libraries for sequences encoding PC-CSF is accomplished utilizing techniques which are described in Maniatis et al. (1982), and in DNA Cloning Vols. I and II (1985). Once clones containing the sequence are identified, the PC-CSF encoding sequence is isolated, cloned, and sequenced. In the event that only a portion of the sequence encoding PC-CSF is isolated, the isolated sequence may be used to construct a probe which will detect clones within the original library which contain overlapping segments of sequence. These sequences, in turn, are cloned and sequenced. This procedure can be repeated until the entire sequence encoding PC-CSF is defined.

The recombinant polynucleotide encoding PC-CSF may then be inserted into an expression vector, and the expression vector used for the transformation of host cells. The general methods for this are described below. The recombinant host cells are selected by cloning, and are cultivated under conditions where the desired protein is expressed. When the protein is not excreted, the cells are harvested and lysed in accordance with conventional procedures, and the protein is isolated in a conventional manner. Where the protein is excreted, the protein may be extracted from the spent nutrient medium.

II.C. General Methods for Recombinant Production of PC-CSF

As discussed above, the general techniques used in sequencing a polypeptide, preparing and probing a cDNA and/or genomic library, in sequencing clones, constructing expression vectors, transforming cells, and the like are known in the art and laboratory manuals are available describing these techniques. However, as a general guide, the following sets forth some sources currently available for such procedures, and for materials useful in carrying them out.

II.C.1. Hosts and Expression Control Sequences

Both prokaryotic and eukaryotic host cells may be used for expression of desired coding sequences when appropriate control sequences which are compatible with the designated host are used. Among prokaryotic hosts, $E.$ $coli$ is most frequently used. Expression control sequences for prokaryotes include promoters, optionally containing operator portions, and ribosome binding sites. Transfer vectors compatible with prokaryotic hosts are commonly derived from for example, pBR322, a plasmid containing operons conferring ampicillin and tetracycline resistance, and the various pUC vectors, which also contain sequences conferring antibiotic resistance markers. These markers may be used to obtain successful transformants by selection. Commonly used prokaryotic control sequences include the Beta-lactamase (penicillinase) and lactose promoter systems (Chang et al., (1977), the tryptophan (trp) promoter system (Goeddel et al., 1980), and the lambda-derived $P_L$ promoter and N gene ribosome binding site (Shimatake et al., 1981) and the hybrid tac promoter (De Boer et al., 1983) derived from sequences of the trp and lac UV5 promoters. The foregoing systems are particularly compatible with *E. coli*; if desired, other prokaryotic hosts such as strains of Bacillus or Pseudomonas may be used, with corresponding control sequences.

Eukaryotic hosts include yeast and mammalian cells in culture systems. *Saccharomyces cerevisiae* and *Saccharomyces carlsbergensis* are the most commonly used yeast hosts, and are convenient fungal hosts. Yeast compatible vectors carry markers which permit selection of successful transformants by conferring prototrophy to auxotrophic mutants or resistance to heavy metals on wild-type strains. Yeast compatible vectors may employ the 2 micron origin of replication (Broach et al., 1983), the combination of CEN3 and ARSI or other means for assuring replication, such as sequences which will result in incorporation of an appropriate fragment into the host cell genome. Control sequences for yeast vectors are known in the art and include promoters for the synthesis of glycolytic enzymes (Hess et al., 1968; Holland et al., 1978), including the promoter for 3 phosphoglycerate kinase (Hitzeman, 1980). Terminators may also be included, such as those derived from the enolase gene (Holland, 1981). Particularly useful control systems are those which comprise the glyceraldehyde-3 phosphate dehydrogenase (GAPDH) promoter or alcohol dehydrogenase (ADH) regulatable promoter, terminators also derived from GAPDH, and if secretion is desired, leader sequence from yeast alpha factor. In addition, the transcriptional regulatory region and the transcriptional initiation region which are operably linked may be such that they are not naturally associated in the wild-type organism.

Mammalian cell lines available as hosts for expression are known in the art and include many immortalized cell lines available from the American Type Culture Collection (ATCC), including HeLa cells, Chinese hamster ovary (CHO) cells, baby hamster kidney (BHK) cells, and a number of other cell lines. Suitable promoters for mammalian cells are also known in the art and include viral promoters such as that from Simian Virus 40 (SV40) (Fiers, 1978), Rous sarcoma virus (RSV), adenovirus (ADV), and bovine papilloma virus (BPV). Mammalian cells may also require terminator sequences and poly A addition sequences; enhancer sequences which increase expression may also be included, and sequences which cause amplification of the gene may also be desirable. These sequences are known in the art. Vectors suitable for replication in mammalian cells may include viral replicons, or sequences which insure integration of the appropriate sequences encoding NANBV epitopes into the host genome.

II.C.2. Transformations

Transformation may be by any known method for introducing polynucleotides into a host cell, including, for example packaging the polynucleotide in a virus and transducing a host cell with the virus, and by direct uptake of the polynucleotide. The transformation procedure used depends upon the host to be transformed. For example, transformation of the *E. coli* host cells with lambda-gt11 containing BB-NANBV sequences is discussed in the Example section, infra. Bacterial transformation by direct uptake generally employs treatment with calcium or rubidium chloride (Cohen, 1972; Maniatis, 1982). Yeast transformation by direct uptake may be carried out using the method of Hinnen et al. (1978). Mammalian transformations by direct uptake may be conducted using the calcium phosphate precipitation method of Graham and Van der Eb (1978), or the various known modifications thereof.

II.C.3. Vector Construction

Vector construction employs techniques which are known in the art. Site-specific DNA cleavage is performed by treating with suitable restriction enzymes under conditions which generally are specified by the manufacturer of these commercially available enzymes. In general, about 1 microgram of plasmid or DNA sequence is cleaved by 1 unit of enzyme in about 20 microliters buffer solution by incubation of 1–2 hr at 37° C. After incubation with the restriction enzyme, protein is removed by phenol/ chloroform extraction and the DNA recovered by precipitation with ethanol. The cleaved fragments may be separated using polyacrylamide or agarose gel electrophoresis techniques, according to the general procedures found in Methods in Enzymology (1980) 65:499–560.

Sticky ended cleavage fragments may be blunt ended using *E. coli* DNA polymerase I (Klenow) in the presence of the appropriate deoxynucleotide triphosphates (dNTPs) present in the mixture. Treatment with S1 nuclease may also be used, resulting in the hydrolysis of any single stranded DNA portions.

Ligations are carried out using standard buffer and temperature conditions using T4 DNA ligase and ATP; sticky end ligations require less ATP and less ligase than blunt end ligations. When vector fragments are used as part of a ligation mixture, the vector fragment is often treated with bacterial alkaline phosphatase (BAP) or calf intestinal alkaline phosphatase to remove the 5'-phosphate and thus prevent religation of the vector; alternatively, restriction enzyme digestion of unwanted fragments can be used to prevent ligation.

Ligation mixtures are transformed into suitable cloning hosts, such as *E. coli*, and successful transformants selected by, for example, antibiotic resistance, and screened for the correct construction.

II.C.4. Construction of Desired DNA Sequences

Synthetic oligonucleotides may be prepared using an automated oligonucleotide synthesizer as described by Warner (1984). If desired the synthetic strands may be labeled with $^{32}P$ by treatment with polynucleotide kinase in the presence of $^{32}P$-ATP, using standard conditions for the reaction.

DNA sequences, including those isolated from cDNA libraries, may be modified by known techniques, including, for example site directed mutagenesis, as described by Zoller (1982). Briefly, the DNA to be modified is packaged into phage as a single stranded sequence, and converted to a double stranded DNA with DNA polymerase using, as a primer, a synthetic oligonucleotide complementary to the portion of the DNA to be modified, and having the desired modification included in its own sequence. The resulting double stranded DNA is transformed into a phage supporting host bacterium. Cultures of the transformed bacteria, which contain replications of each strand of the phage, are plated in agar to obtain plaques. Theoretically, 50% of the new plaques contain phage having the mutated sequence, and the remaining 50% have the original sequence. Replicates of the plaques are hybridized to labeled synthetic probe at temperatures and conditions which permit hybridization with the correct strand, but not with the unmodified sequence. The sequences which have been identified by hybridization are recovered and cloned.

II.C.5. Hybridization with Probe

DNA libraries may be probed using the procedure of Grunstein and Hogness (1975). Briefly, in this procedure, the DNA to be probed is immobilized on nitrocellulose filters, denatured, and prehybridized with a buffer containing 0–50% formamide, 0.75 M NaCl, 75 mM Na citrate, 0.02% (wt/v) each of bovine serum albumin, polyvinyl pyrrolidone, and Ficoll, 50 mM Na Phosphate (pH 6.5), 0.1% SDS, and 100 micrograms/ml carrier denatured DNA. The percentage of formamide in the buffer, as well as the time and temperature conditions of the prehybridization and subsequent hybridization steps depends on the stringency required. Oligomeric probes which require lower stringency conditions are generally used with low percentages of formamide, lower temperatures, and longer hybridization times. Probes containing more than 30 or 40 nucleotides such as those derived from cDNA or genomic sequences generally employ higher temperatures, e.g., about 40°–42° C., and a high percentage, e.g., 50%, formamide. Following prehybridization, 5'-$^{32}P$-labeled oligonucleotide probe is added to the buffer, and the filters are incubated in this mixture under hybridization conditions. After washing, the treated filters are subjected to autoradiography to show the location of the hybridized probe; DNA in corresponding locations on the original agar plates is used as the source of the desired DNA.

II.C.6. Verification of Construction and Sequencing

For routine vector constructions, ligation mixtures are transformed into *E. coli* strain HB101 or other suitable host, and successful transformants selected by antibiotic resistance or other markers. Plasmids from the transformants are then prepared according to the method of Clewell et al. (1969), usually following chloramphenicol amplification (Clewell, 1972). The DNA is isolated and analyzed, usually by restriction enzyme analysis and/or sequencing. Sequencing may be by the dideoxy method of Sanger et al. (1977) as further described by Messing et al. (1981), or by the method of Maxam et al. (1980). Problems with band compression, which are sometimes observed in GC rich regions, are overcome by use of T-deazoguanosine according to Barr et al. (1986).

II.D. Preparation of Antibodies Against NA Cells

NA cells from a heterologous species may be used to produce antibodies, both polyclonal and monoclonal. If polyclonal antibodies are desired, a selected mammal which is of a species which is heterologous to the subject NA cells (e.g., mouse, rabbit, goat, horse, etc.) is immunized with a preparation of NA cells, or lysed NA cells, preferably in the presence of adjuvant. Serum from the immunized animal is collected and treated according to known procedures. If serum containing polyclonal antibodies to NA cells contains antibodies to other cell types, the polyclonal antibodies can be purified by immunoaffinity chromatography. Techniques for producing and processing polyclonal antisera are known in the art, see, for example, Mayer and Walker (1987).

Monoclonal antibodies directed against NA cell specific epitopes can also be readily produced by one skilled in the art. The general methodology for making monoclonal antibodies by hybridomas is well known. Immortal antibody-producing cell lines can be created by cell fusion, and also by other techniques such as direct transformation of B lymphocytes with oncogenic DNA, or transfection with Epstein-Barr virus. See, e.g., M. Schreier et al. (1980); Hammerling et al. (1981); Kennett et al. (1980); see also, U.S. Pat. Nos. 4,341,761; 4,399,121; 4,427,783; 4,444,877; 4,452,570; 4,466,917; 4,472,500; 4,491,632; and 4,493,890. Panels of monoclonal antibodies produced against NA cells can be screened for specificity to NA cells, using known techniques, including, for example, those relying on flow cytometry. In particular, the screening will include testing the antibody against a variety of more mature cell types, including those listed in Tables 1 and 2, supra. Antibodies which are specific for NA cells in that they do not bind to the more mature cell types are selected. In addition, the antibodies can also be screened for various properties; i.e., for isotype, epitope affinity, etc.

Antibodies, both monoclonal and polyclonal, which are directed against NA cells, are useful for the identification and isolation of these cells.

II.E. Methods of Isolating NA Cells

The present method contemplates any method employing antibodies, preferably monoclonal antibodies, to separate NA cells from more mature cells in bone marrow or other lymphohematopoietic organs. Generally, a cell suspension prepared from tissue containing hematopoietic cells (for example, bone marrow, spleen, bursa), is brought into contact with a preparation of anti-NA cell antibodies. Cells which have been bound by the antibodies are separated from unbound cells by any means known to those skilled in the art.

Various methods of separating antibody-bound cells from unbound cells are known. For example, the antibody-cell complex can be labeled, and the cells separated by a mechanical cell sorter that detects the presence of the label. Fluorescence-activated cell sorters are well known in the art. In a preferred embodiment, the anti-stem cell antibody is attached to a solid support. Various solid supports are known to those of skill in the art, including, but not limited to agarose beads, polystyrene beads, hollow fiber membranes, and plastic petri dishes. Cells that are bound by the antibody can be removed from the cell suspension by simply physically separating the solid support from the cell suspension.

Selective cytophoresis can be used to produce a cell suspension from a hematopoietic organ. For example, marrow can be harvested from a donor by any appropriate means. The marrow can be processed as desired, depending mainly upon the use intended for the recovered cells. The suspension of marrow cells is allowed to physically contact the monoclonal antibodies that recognizes an antigen on the NA cells; the antibodies are linked to a solid phase. The exact conditions and duration of incubation for the solid phase-linked antibodies with the marrow cell suspension depends upon several factors specific to the system employed. The selection of appropriate conditions, however, is within the skill of the art.

After an appropriate time for binding, the unbound cells are eluted or washed away with physiologic buffer. The bound cells are then separated from the solid phase by any appropriate method. For example, bound cells may be eluted by vigorous agitation. Alternatively, they may be eluted by enzymatic nicking or digestion of a "spacer" sequence which binds the solid phase and the antibody.

The eluted, enriched fraction of cells may then be washed with a buffer and either cryopreserved in a viable state for later use, using conventional techniques of cryopreservation, or immediately infused intravenously into a transplant recipient. Alternatively, the cells may be kept in cell culture for later use. Conditions suitable for culturing cells are within the skill of the art, and conditions under which NA cells have been maintained in culture are described in the Examples.

II.F. Methods of Therapy

The above cell suspensions of NA cells can be used in therapeutic methods, such as progenitor cell transplantation, as well as others that are readily apparent to those of skill in the art. For example, such cell populations suspended in pharmaceutically excipient(s) can be administered directly by I.V. injection to an individual requiring cell replacement therapy in an amount sufficient to reconstitute the individual's hematopoietic and/or immune system. Pharmaceutically acceptable excipients include, for example, physiologically buffered isotonic salt solutions, such as saline, and isotonic solutions of glucose or dextrose. Other components of the cell suspension may be those listed below for PC-CSF. Precise effective quantities can be readily determined by those skilled in the art and will depend, of course, upon the exact condition being treated by the therapy. In many applications, however, an amount containing approximately the same number of NA cells found in one-half to one liter of aspirated marrow should be adequate.

Therapeutic methods for hematopoietic disorders in an individual may also include treating the individual with PC-CSF. The treatment with PC-CSF may be alone, or in conjunction with other therapeutic methods, for example, cell replacement or augmentation with NA cells. The PC-CSF may be prepared as injectables, either as liquid solutions or suspensions; solid forms suitable for solution in, or suspension in, liquid prior to injection may also be prepared. The preparation may also be emulsified, or the protein encapsulated in liposomes. The active PC-CSF is often mixed with excipients which are pharmaceutically acceptable and compatible with the active ingredient. Suitable excipients are, for example, water, saline, dextrose, glycerol, ethanol, or the like and combinations thereof. In addition, if desired, the PC-CSF preparation may contain minor amounts of auxiliary substances such as wetting or emulsifying agents, and pH buffering agents. The preparations are conventionally administered parenterally, by injection, for example intravenously, subcutaneously, or intramuscularly. Additional formulations which are suitable for other modes of administration include suppositories and, in some cases, oral formulations. Materials suitable for these formulations are known by those of skill in the art. The PC-CSF is administered in a manner compatible with the dosage formulation, and in such amount as will be therapeutically effective. The quantity to be administered depends on the hematopoietic disorder and the subject to be treated. The PC-CSF may be given in a single dose schedule, or preferably in a multiple dose schedule. A multiple dose schedule is one in which a primary treatment may be 1-10 separate doses, followed by other doses given at subsequent time intervals required to maintain and or reenforce the therapeutic response. The dosage regimen will also, at least in part, be determined by the need of the individual and be dependent upon the judgment of the practitioner.

The following examples are provided to illustrate specific embodiments of the present invention. The examples are included for illustrative purposes only and are not intended to limit the scope of the present invention.

Example 1

Isolation of Adherent Cell Lines

Bone marrow cultures were derived from bone marrow aspirates from two Holstein calves. The bone marrow cells were collected in 2x citrate from the iliac crest of two anesthetized calves, which were both less than 1 year old. The bone marrow samples were washed free of citrate using Minimal Essential Medium (MEM) and centrifuged at 2,000 rpm for 15 minutes. The cell pellet was resuspended in MEM and the cell suspension was layered onto a ficollhypaque density gradient and centrifuged at room temperature (rt) for 30 min. at 2,000 rpm. Following centrifugation the cells at the interface of the gradient were collected, diluted in MEM, and again centrifuged for 10 min. at 1,000 rpm. The cells were washed two additional times. Following the final wash, the cells were resuspended in RPMI-1640 supplemented with 10% fetal bovine serum (FBS). The cell suspension was adjusted to give a final cell concentration of $2 \times 10^6$ cells/ml. The bone marrow cell suspensions were then seeded into 100 mm diameter petri dishes (Costar) at a concentration of $1 \times 10^7$ cells/plate in a volume of 15 ml of growth media (RPMI plus 10% FBS). The culture plates were then incubated at 37° C. in a humidified incubator in an atmosphere of 5% $CO_2$ in air. The two resulting cultures were designated B.BM.1 and B.BM.2.

Between two to three weeks after culture, an adherent cell population which grew on the surface of the petri dish appeared. When these cells reached confluency, they were passaged into T 75 $cm^2$ flasks as follows. Petri dishes containing confluent monolayers of adherent cells were washed free of excess growth media, using a solution of versene and trypsin (5%). After the second wash, 2.0 ml of the versene-trypsin solution was added, the plates were incubated at 37° C. for 5 min, and the plates were examined to be certain that the cells had detached from the plate surface. A single cell suspension was obtained by the addition of 10 ml of RPMI containing 10% FBS to the plate, followed by agitation. The cell suspension was centrifuged at 1,000 rpm for 8 min., and the supernatant was discarded. The cell pellet was resuspended in fresh growth medium, and the cell numbers adjusted to $2 \times 10^6$ cells/ml. The cell suspension was then added to sterile T 75 $cm^2$ flasks at a concentration of $4 \times 10^6$ cells/flask in 40 ml of media. The cells were then serially passaged as an adherent population using Dulbecco's Minimal Essential Medium supplemented with 10% fetal bovine serum.

Further growth of adherent cell populations of B.BM.1 and B.BM.2 for two months without passaging, allowed the growth of a population of NA cells which replicated upon the surface of the adherent cell. Both bottles of cells were passaged, and an aliquot of B.BM.2 stored was stored in liquid nitrogen. B.BM.2 was maintained in culture as a mixed population of adherent (stromal) cells and NA cells.

EXAMPLE 2

Isolation of NA Cell Lines

During the original cultivation and maintenance of NA cells, it was noticed that the NA cells were dependent upon physical attachment to the stroma monolayers. If the NA cell was separated by placement in a chamber which only allowed "communication" via soluble factors but not by physical attachment, the NA cells died. However, the stromal area beneath the chamber generated small colonies of NA cells.

Original attempts to obtain a proliferating NA cell population in the absence of stroma failed. However, by utilizing conditioned media from the original B.BM.1 cultures, NA cell lines which are free of stromal cells have been isolated and maintained in culture. These cell lines are derived from several species. In certain cases, i.e., with the human and pig bone marrow cultures, it was necessary to treat the bone marrow cultures twice with conditioned medium derived from bovine bone marrow cultures to obtain the NA cell cultures. In these cases, the treatment with the conditioned medium was 4 days apart.

Example 3

Characterization of Bone Marrow Derived Cell Lines: Structural Analysis

Structural analysis of the cell lines was performed using thin-section electron microscopy. Stroma cells and NA cells were prepared separately for the examination. NA cells were removed from the cultures by extensive washing and pipetting, and the stroma cells were detached by trypsinization. Cell pellets were prefixed in 2½% gluteraldehyde in 0.1M phosphate buffered saline (PBS), pH 7.1, and postfixed in 1% $OsO_4$ PBS. Ultrathin sections were stained with uranyl acetate and lead citrate, and examined in a Philips electron microscope at 60 kV.

The stromal cells, detached by trypsinization, appeared to have a ruffled membrane, due to numerous filipodia of varying length and thickness. The cell body measured 20–25 millimicrons in diameter. The nuclei were very polymorphic and euchromatic with a narrow band of heterochromatin along the nuclear membranes. A large nucleolus was usually present. The cytoplasm appeared electron dense and organelle-rich, the latter comprising a well-developed Golgi-region, elongated mitochondria with a very dense matrix, numerous vesicles with a granular and filamentous content and abundant rough endoplasmic reticulum (RER). The RER could be distended, containing a dense, proteinaceous material. In many cells, patches of filamentous material occupied an area in the periphery of the cytoplasm. This may constitute the "adherence-apparatus" of the cells.

The NA cells in the original culture system were of a uniform size and morphology, except for a few cells in mitosis and a rare cell of pro-granulocytic character. The majority of NA cells were approximately 12–16 millimicron in diameter. The cells appeared to have a rounded or bilobed nucleus, which was usually euchromatic, with a large membrane-associated nucleolus. The cytoplasm was relatively poor in organelles, which were comprised of a few strands of RER, varying numbers of large, often distended mitochondria, and a few small electron dense granules and multivesicular bodies. However, the cytoplasm had an electron dense appearance due to numerous free ribosomes and polyribosomes.

NA cells in the secondarily induced cultures, which were prepared as described in Example 2, appeared to be more heterogenous, both in size and morphology, although they all resembled cells of monocyte-macrophage lineage. The nuclear morphology resembled that of the primary culture, but the nuclei were often rich in heterochromatin. The cytoplasm was characterized by abundant free ribosomes and polyribosomes, but in addition, many cells were well equipped with organelles. A prominent Golgi zone was observed in many cells, comprised of large stacks of flat saccules and associated vesicles. The RER was also more abundant in these cells than in those of the original culture system, and signs of phagocytosis (exo/endo, auto) were evident in some cells. Some of the cell heterogeneity may reflect differences in cell age, rather than differences in differentiation pathways, since signs of senescence were also evident in occasional cells, and since the phenotypic profile of these cells appears to be homogeneous (see Example 4, and Table 1).

Example 4

Characterization of Bovine Bone Marrow Derived Cell Lines: Phenotypic Analysis

The phenotypic profile of the bone marrow cell lines of bovine origin, B.BM.1. and B.BM.3, were studied using membrane fluorescence in a semi-quantitative procedure and using flow cytometric analysis. These cell lines are NA cell lines.

The phenotypes of the two bovine cell lines, B.BM.1 and B.BM.3, were analyzed using a panel of monoclonal antibodies that are specific for T cell subsets, MHC class I and class II antigens, macrophage/monocytes, null cells (non T/non B), and B lymphocytes. The panel of monoclonal antibodies was obtained from W. C. Davis, of Washington State University, Pullman, Wash. The antibodies used, and their specificities are shown in Table 1.

Flow cytometric analysis was performed as follows. The bone marrow cells were pelleted (1,000 rpm for 8 min.) and resuspended at a concentration of $2 \times 10^7$ in phosphate buffered saline (PBS G) containing 0.2% gelatin (Sigma Chem. Co., St. Louis, Mo.), 1 mM sodium azide and 2.0% normal rabbit serum (Cooper biomedical, Malvern, Pa.). In order to study the surface phenotype, 50 microliters of the cell suspension was added to 50 microliters of the appropriate monoclonal antibody in a 96-well flat-bottomed microtiter plate and incubated for 30 minutes at 4° C. The cells wee washed three times with ice-cold PBS G and then incubated for 30 minutes at 4° C. with 100 microliters of FITC-labeled $F(ab^1)_2$ goat anti-mouse immunoglobulin (heavy and light chain specific, Cooper Biomedical, Malvern, PA) diluted 1:75 with PBS G. After incubation, the cells wee washed three times with PBS G and then fixed in a 2% solution of formaldehyde in PBS G. The cell preparations were placed in the dark at 4° C. until analyzed. Cell aggregates were removed from all samples by filtering through a 62 millimicron nylon-monofilament mesh (Small Parts Inc., Miami, Fla.) immediately prior to Fc analysis. The appropriate controls were included to detect non-specific labeling due to Fc receptor (FcR) binding. In these controls the bone marrow cells were reacted with either FITC labeled $F(ab^1)_2$ alone, or with an isotype-matched monoclonal antibody specific for an irrelevant antigen.

The FITC-labeled bone marrow cells were analyzed with a Coulter Electronics Ltd. EPICS V flow cytometer. Data from 20,000 cells were collected to analyze the patterns of monoclonal antibody reactivity. Two parameter analysis of forward angle light scatter (FALS) versus 90o light scatter (LI 90) was used to eliminate dead cells and debris from the population under analysis. The fluorescent data were collected as both scatter plots of FALS versus fluorescence, and as histograms of fluorescence versus cell number. The percentage of positive cells was determined using the immunoprogram (Coulter Electronics Ltd., MDADS System, Version 3.1).

The flow cytometric analyses of B.BM.1 and B.BM.3 showed that these cell lines express neither the T cell or B cell markers, nor do they express monocyte/macrophage markers. They also lack expression of MHC class II (IA) antigen, and of the $T_4$ helper cell antigen. However, all of the cells express the MHC class I antigen.

In order to further characterize the cells, they were subjected to immunocytochemical studies. Immunocytochemical demonstration of surface-membrane and cytoplasmic phenotype-markers was done as described in detail by H. Bielefeldt Ohmann (1987) J. Histochem. Cytochem. 35:627–633. Briefly, leukocytic antigens were detected using a panel of immune monoclonal antibodies (Table 1) by incubating cytospin preparations on poly-L-lysine coated slides with the appropriate dilution of the antibodies in question for 1 h. Following 3 washing steps, a rabbit-anti mouse-Ig was applied, and incubation was resumed for ½ h, followed by washing. Alkaline phosphatase-anti alkaline phosphatase complexes were then applied. After a final washing sequence, slides were incubated with the substrate (2 micrograms AS-MX phosphate in 0.2M Tris-buffer, pH 8.2, 1 mM Lidocaine and 1 mg fast TR salt). After counterstaining with methyl green the cell preparations were mounted in aqueous gelatins and examined by light microscopy.

The results of the phenotypic analysis using immunocytochemical methods is presented in Table 1. These results indicated that, in agreement with the flow cytometric analyses, the B.BM.1 and B.BM.3 cells lacked T cell markers, MHC class II antigens, B cell markers, and some macrophage markers. However, in contrast to the flow cytometric analysis, the analyses using immunocytochemical methods showed that the null cell marker, B7A, was present. Also present were those of monocyte subpopulations, B18A, DH59B, H18A, CA137A, and CH16A. The immunocytochemical method detects intracellular as well as surface bound antigens, while the flow cytometric method monitors only surface bound antigens. The differences detected may be related to this difference in specificity in the two methods.

TABLE 1

Phenotypic Profile of Bovine Bone Marrow Culture Cells Determined by Immunocytochemical Methods

| Designation of Monoclonal Antibody | Specificity | Reactivity With NA Cells | (% TVE Cells) Stroma Cells |
|---|---|---|---|
| B7A | Null cells | 99.0 | NT |
| B18A | Granulocytes, monocyte subset T-lymphocyte subset (?) | 92.7[b] | NT |
| DH59B | Blood monocytes | 97.9 | NT |
| M718 | Mature macrophages | 0.0 | NT |
| TH14B | MHC Class II | 0.0 | 0 |
| H42A | MHC Class II | 0.0 | 0 |
| CH128A | T-lymphocytes (E-roset) | 0.0 | 5.5[a] |
| RH12A | MHC Class I | 5.2[b] | 100[b] |
| BIg73 | B-lymphocytes (IgH) | <2 | 0 |
| GS5A | B + T lymphocyte subset | ?[c] | ? |
| BAQ44 | B-lymphocytes | ? | ? |
| H18A | Monocyte-subset (?) | 100 | NT |
| RH16A | MHC Class I | −/? | 100[b] |
| B29A | Pan T-lymphocyte | 0 | NT |
| CH137A | Monocyte subset | 95.7 | NT |
| CH16A | Monocyte subset | 94.0 | NT |
| IL-22 | Macrophage-subpopulaton (mature cells) | ≦1[d] | NT |
| IL-23 | — | ≦1[d] | NT |
| IL-24 | — | ≦1[d] | NT |
| E4C | T-lymphocyte subset | 0.0 | NT |
| E40C | — | 0.0 | NT |
| HUH27 | Granulocytes (neutroph.) | 0.0 | NT |
| BAQ4A | NonT, NonB cells | ≦1[d] | NT |
| BAS9A | B-lymphocytes | ? | NT |
| H34A | MHC Class II | 0.0 | 0 |

[a]Antigen only expressed intracellularly. Only giant cells positive.
[b]Weak antigen reaction (low staining intensity).
[c]Weak, questionable reaction in/on some cells.
[d]Positive cells only among giant cells.

Cytospin preparations on poly-L-lysine coated slides were fixed in 10% acetone in 0.85% NaCl with 0.05% BSA for 10 min and stained by a 3-step immunocytochemical method described in detail elsewhere (Breteheldt Ohmann, (1987)) employing the tested murine monocolonal antibody complexes (the latter two reagents from DAKOPATTS a/w, Glostrap, DK). The chromagen was naphtol-XM-phosphate. A minimum of 100 cells were counted per slide.

Example 5

Characterization of Human Bone Marrow Derived Cell Lines: Phenotypic Analysis

The phenotypic analysis of the NA human cell line, HU.BM.2, was studied using flow cytometric analysis. The flow cytometric analysis was performed as described in Example 4. The monoclonal antibodies used for the phenotypic analysis were directed to HLA class I and class II determinants, human T cell markers, macrophage/monocyte markers, B cell markers, and some tumor cell lines.

Example 6

Characterization of the NA Bone Marrow Cell Lines

The Effect of Cytokines on Function

In order to ascertain whether the NA bone marrow cell lines belonged to either the lymphoid or monocyte/macrophage lines, or if they were early progenitor cells, i.e., myeloid-lymphoid stem cells, an analysis of the effect of cytokines on the cell lines B.BM.3., HU.BM.2, and MU.BM.2 was performed. The results of the studies, discussed below, showed that B.BM3, HU.BM.2., and MU.BM.2 did not have functions which would identify them as a member of either lineage.

Effect of r-IL-2

The addition of interleukin 2 (IL-2) to lymphoid cells principally of the Natural killer (NK) cell population induces or enhances this cell to become cytolytic for tumor cell targets. Preincubation of B.BM.3, HU.BM.2, and MU.BM.2 in the presence of human recombinant IL-2 for 24–48 hours prior to their use in a cytotoxicity assay ($^{51}$Cr-release assay) using K562 as a target source did not facilitate these NA cells into becoming lymphokine activated killer (LAK) cells. Cells without prior incubation with IL-2 also lacked ability to kill tumor cell targets.

Effect of IFN-gamma, IFN-alpha, and TNF-alpha

NA bone marrow cells, B.BM.3, HU.BM.2, and MU.BM.2, were preincubated for 24 and 48 hours with the following varying dilutions (micrograms/ml) of recombinant bovine gamma-interferon (IFN-gamma), alpha-interferon (IFN-alpha), and alpha-tissue necrosis factor (TNF-alpha): 1 microgram, 0.1 microgram, 0.001 microgram, and 0.0001 microgram. After incubation, the cells were assessed for their ability to mediate luminol-enhanced chemiluminescence in the presence of opsonized Zymosan. This assay was used to monitor the induction of reactive oxygen species. Cells subjected to this same pretreatment were also tested for their ability to migrate (chemotaxis) towards activated bovine serum, which is a putative source of C5a (the chemotactic split product of the C5 complement component). C5a is a potent chemotactic peptide.

The results showed that treatment with IFN-gamma, IFN-alpha, and TNF-alpha caused neither an induction of the production of reactive oxygen species, nor an induction of vectorial migration to putative C5a, by the NA bone marrow cell preparations. The untreated cells also did not exhibit these functions.

Example 7

The Effect of Cytokines on the Morphology of NA Bone Marrow Cell Lines

The effect of cytokines on the morphology of NA bone marrow cell lines B.BM.3, HU.BM.2, and MU.BM.2, was monitored using a clonogenic assay procedure. The clonogenic assay was performed as described in Example 16, infra, except that PC-CSF was replaced as the stimulant by bovine IFN-gamma, IFN-alpha, and TNF-alpha, at the following dilutions (microliters/ml): 1 microgram, 0.1 microgram, 0.01 microgram, and 0.001 microgram.

The results of the clonogenic assay procedure showed that IFN-gamma, IFN-alpha, and TNF-alpha did not induce a change in the number of colonies, nor in the morphology of the cells and types of colonies observed.

Example 8

The Effect of NK Cells on NA Bone Marrow Cell Lines

One of the major roles for Natural Killer effector (NK) cells, may be the regulation of hematopoiesis by removing or regulating the pluripotent stem cell population in the bone marrow (Barlozzaci et al., 1987). The cytocidal effect of NK cells on bone marrow cells was monitored using a standard $^{51}$CR-release microcytoxicity assay in which the NA bone marrow cells (B.BM.3, HU.BM.2, and MU.BM.2) were $^{51}$Cr-labeled and used as targets for NK associated with peripheral blood lymphocytes from human, bovine, and murine spleen cultures. The effector cells (NK) were assayed for cytolytic activity in the presence and absence of recombinant IL-2.

Figure 1B:
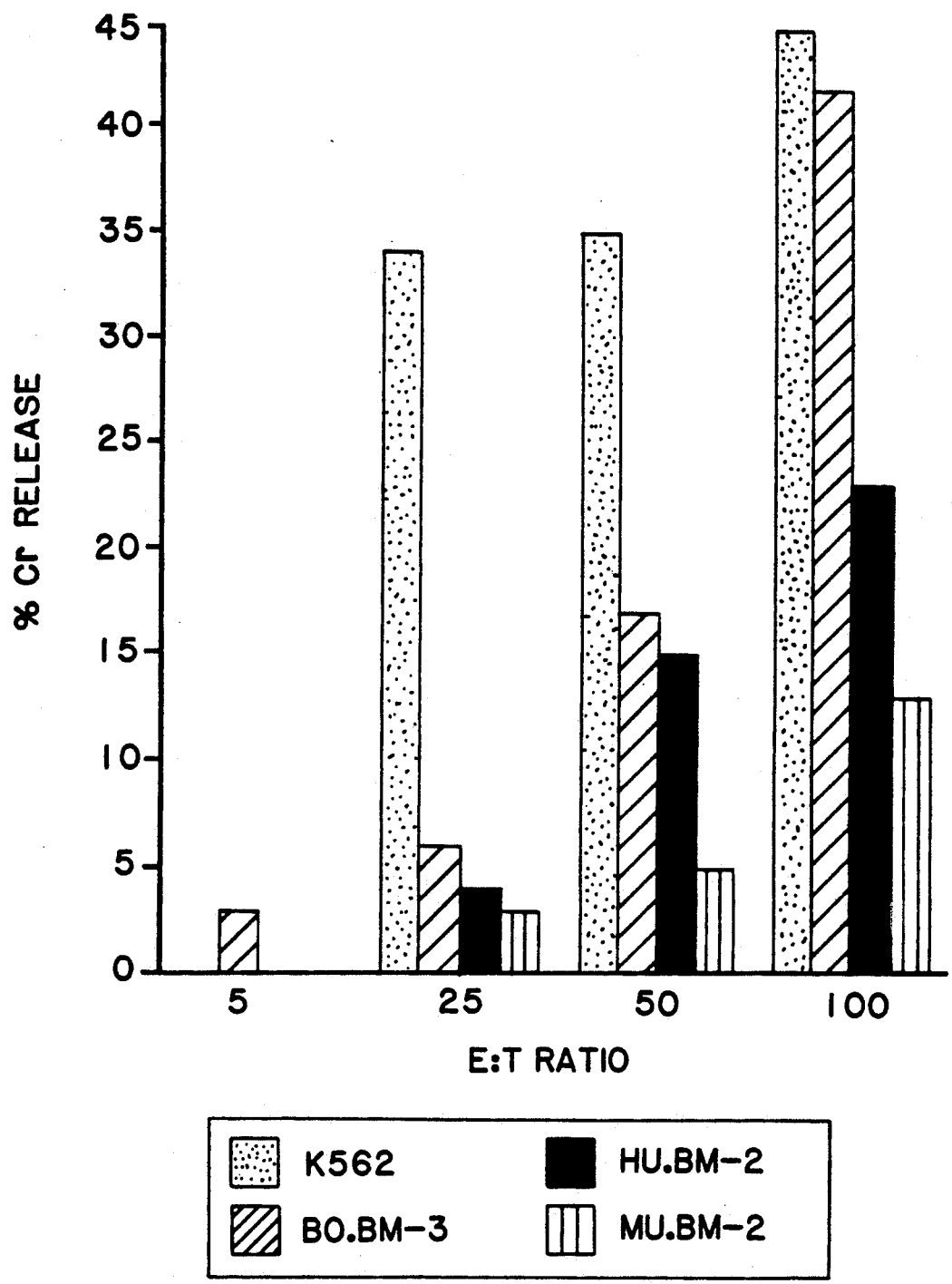
Figure 2A:
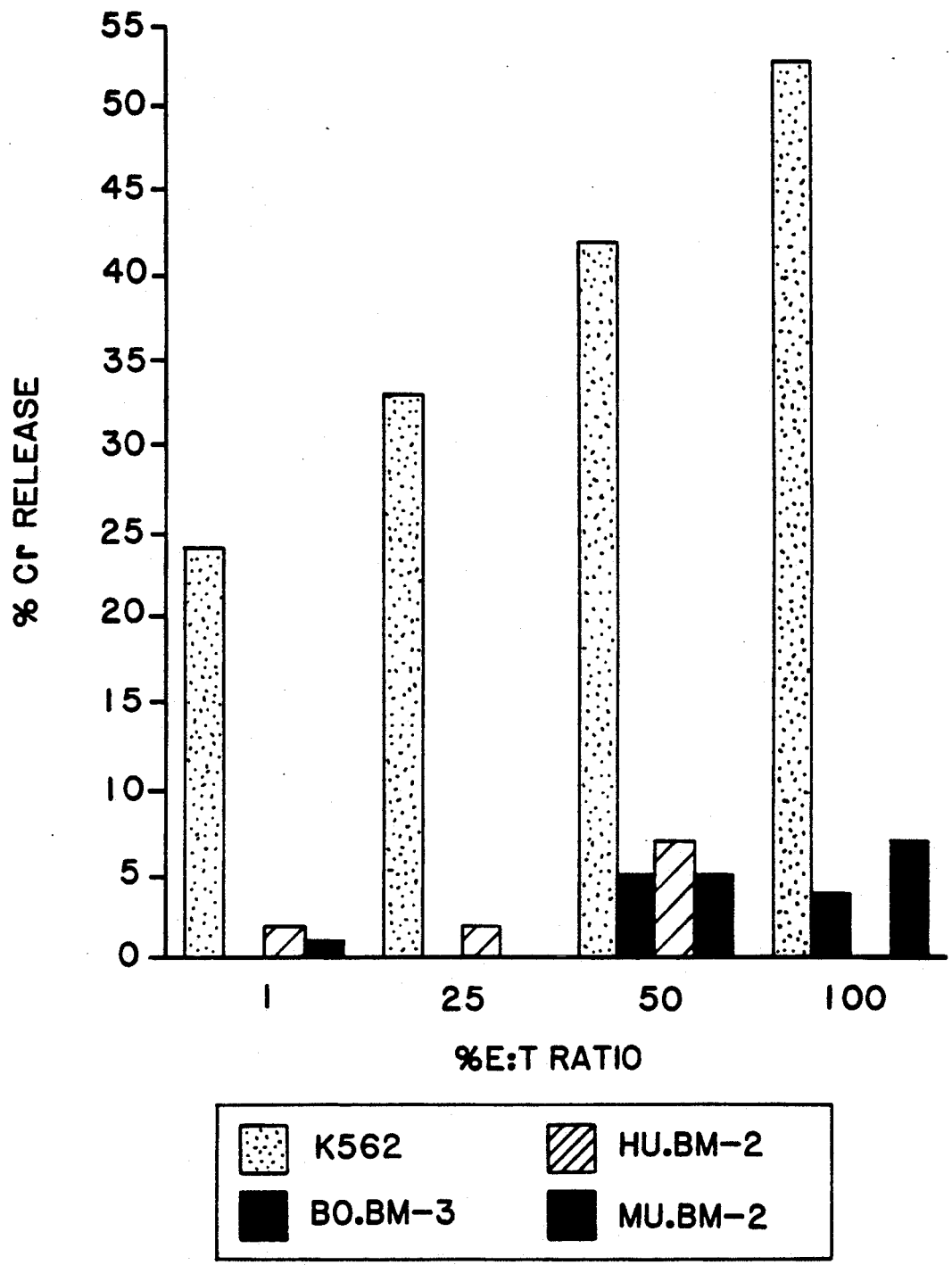
FIGS. 2A, 2B are graphs which shows the cytotoxic effect of human NK cells on human NA cells.
Figure 2B:
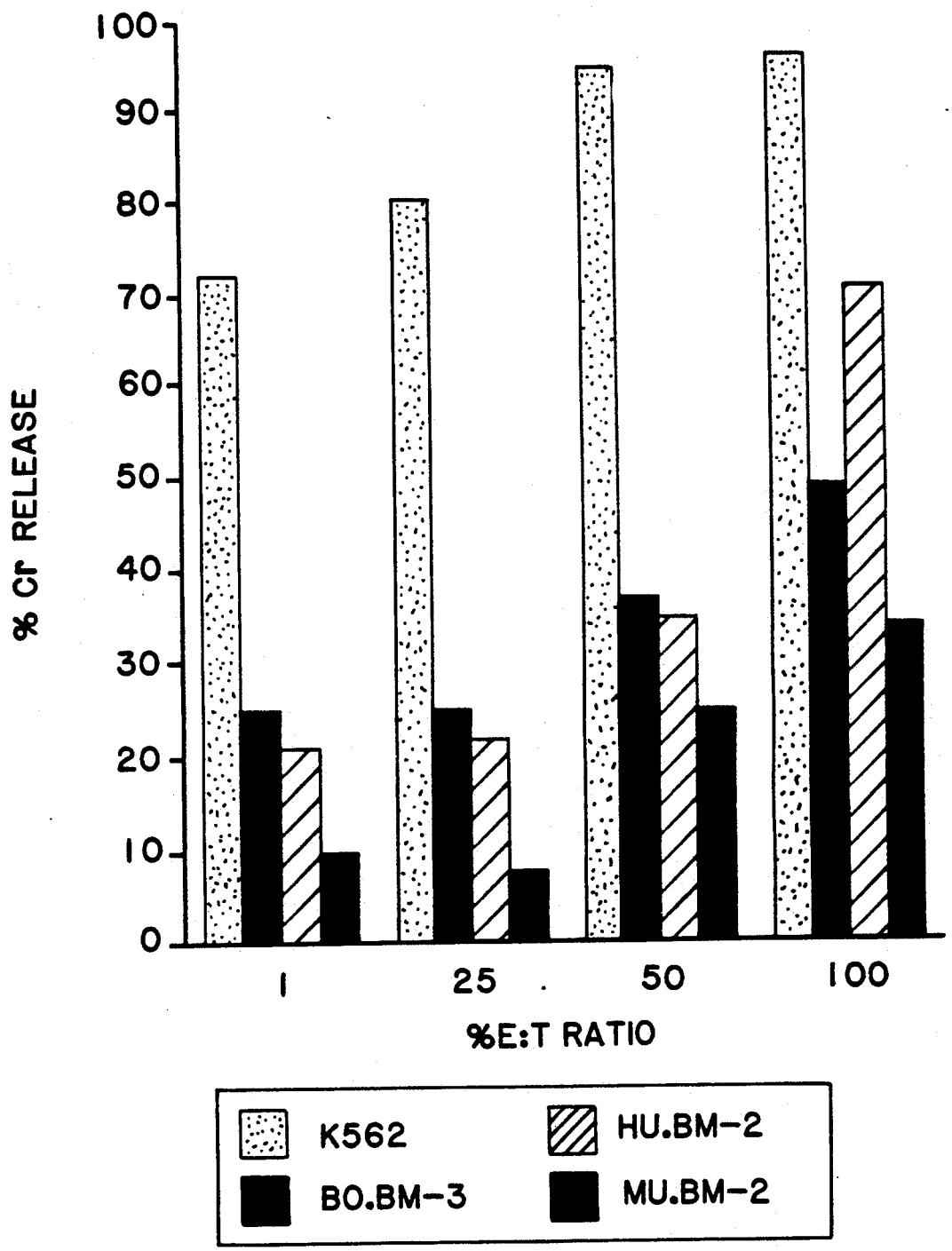
Figure 3A:
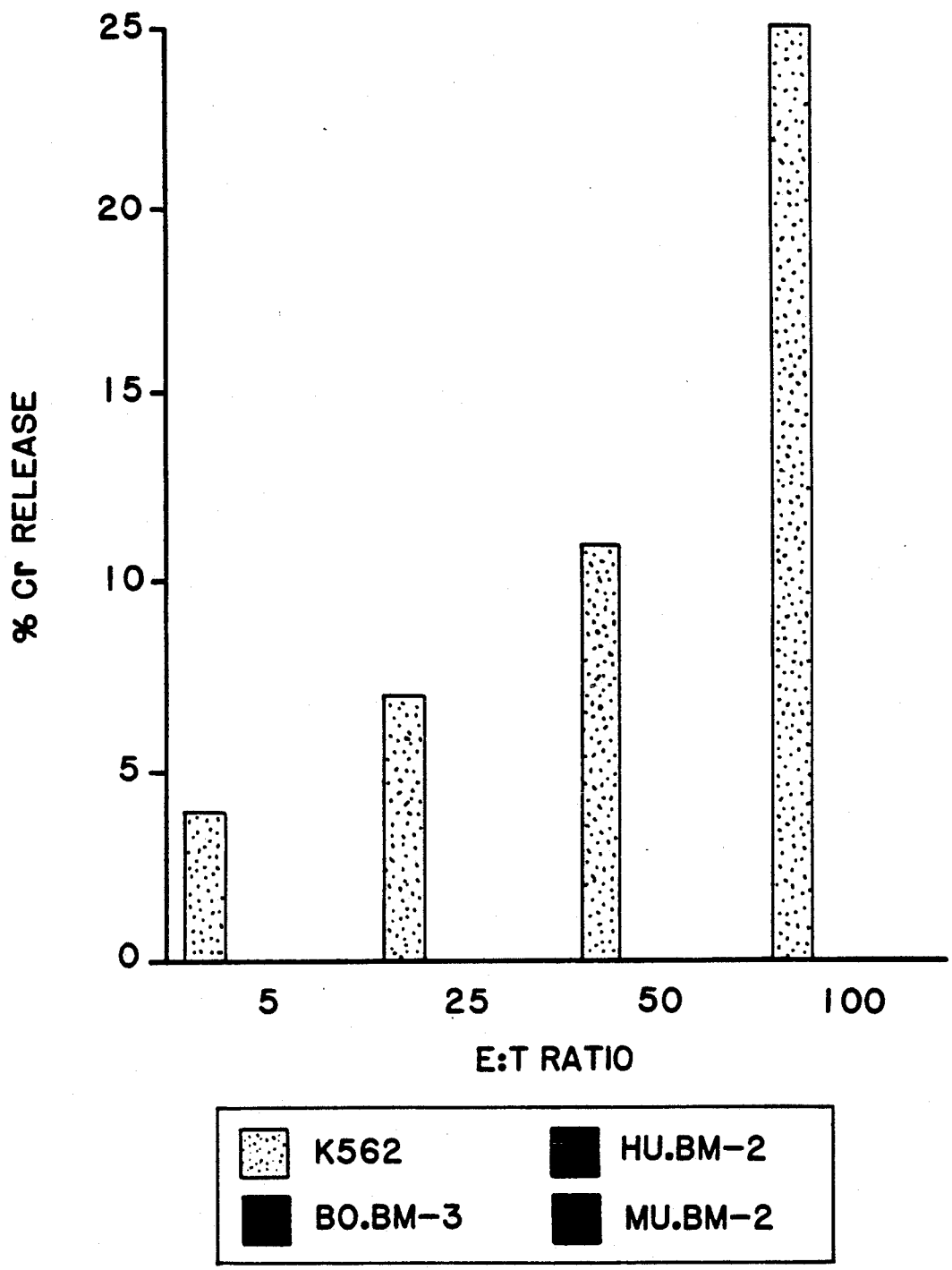
FIGS. 3A, 3B are graphs which shows the cytotoxic effect of murine NK cells on murine NA cells.
Figure 3B:
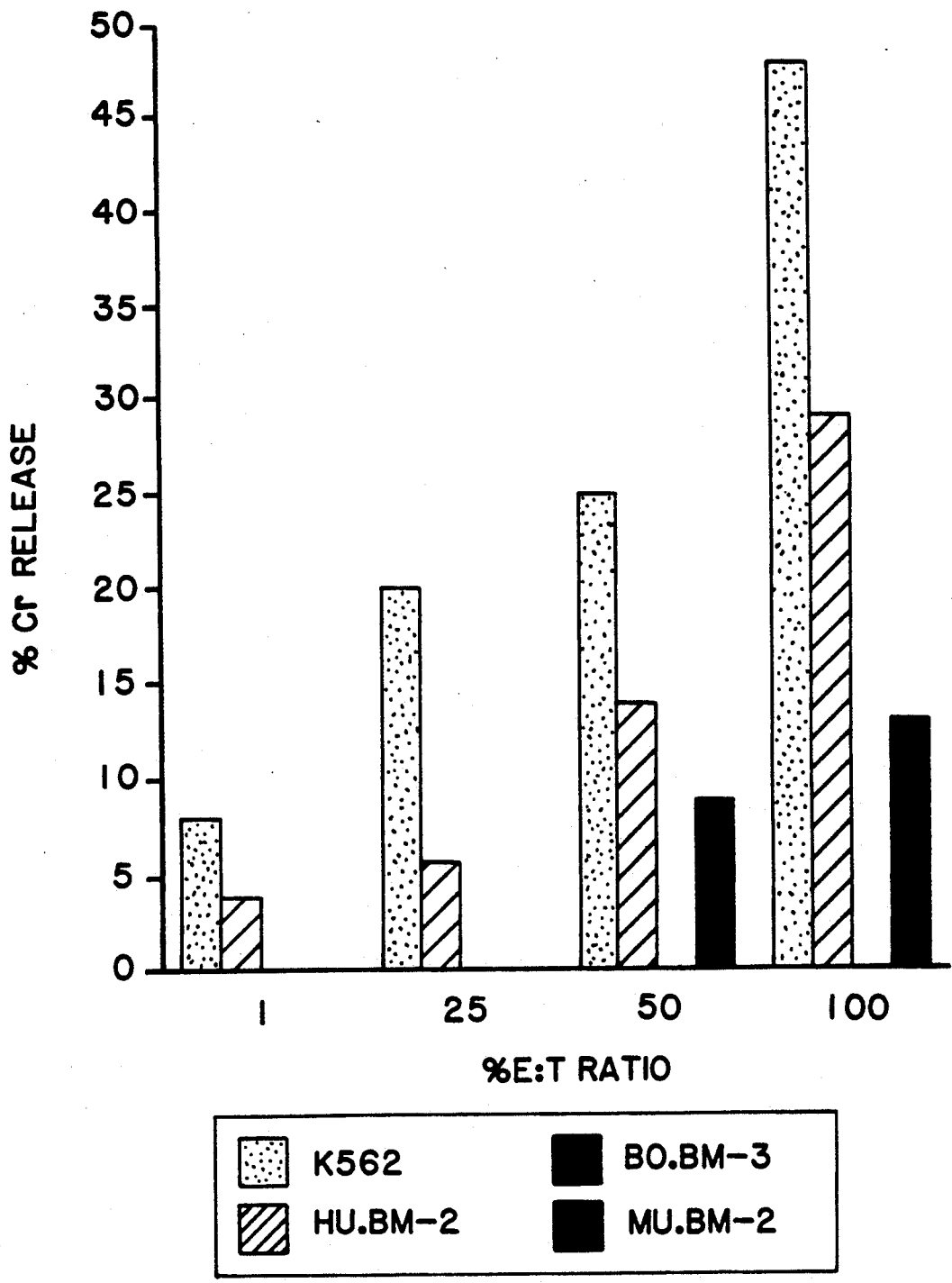

As seen from the results in FIGS. 1, 2, and 3, respectively, the bovine, human, and to a lesser extent the murine bone marrow cell lines act as targets for non-MHC-restricted lysis by the putative bovine, human, and murine NK cells. The lysis is significantly enhanced when the NK cells have been treated with IL-2 for 48 hours prior to their interaction with the adherent bone marrow cells.

It is noteworthy that pretreatment of bone marrow cells with recombinant IL-2 does not induce them to have any effector function against themselves, or against tumor targets, such as K562.

Example 9

Homing of the NA Bone Marrow Cell Lines to Hematopoietic Tissue

Murine NA bone marrow cells, MU.BM.2, were labeled with $^{32}$P, and were inoculated intravenously into mice. At appropriate times post inoculation, the mice were sacrificed and placed upon X-ray film. The exposed X-ray films were developed and examined to determine if any of the $^{32}$P labeled material was present in hematopoietic tissue in the inoculated mice. The results showed that the amount of $^{32}$P label in the mouse bone marrow row was detectable at two hours, and substantial at 30 hours, suggesting that the labeled cells had homed to the murine hematopoietic tissue.

Example 10

Hematopoietic Potential of Bone Marrow Cell Lines: CFU-S (Colony Forming Units-Spleen) Assay The CFU-S assay measures the hematopoietic potential of pluripotent stem cells.

The CFU-S assay was performed in lethally irradiated mice. The mice, which were BALB/c, were given a dose of V irradiation of 1200 rads/total body (300 rads/minute). This dose was previously determined to be the LD$_{50}$ dose. The results showed that inoculating irradiated mice with as few as 1000 MU.BM.1 cells generated numerous within the spleen. After 13 days, mice injected with either $10^3$ or $10^6$ cells formed per mouse, 10 colonies and more than 30 colonies, respectively.

The general histomorphological appearance of the spleens of the inoculated mice suggested immune-reactivity. This classification was based upon the well developed secondary follicles and wide, cell-rich periarteriolar lymphatic sheaths (PALS). This expansion of the "white pulp" was accompanied by a diminution of the "red pulp".

Small assemblances of blastoid cells, which were 2-4 times larger than follicular lymphocytes, were interspersed between the elements of the white pulp, either deep in the spleen parenchyma or directly under the capsule. The smaller cell colonies apparently were not separated from the normal spleen parenchyma by non-lymphoid structures (connective tissue or endothelium). The cells in these smaller colonies appeared homogeneous containing abundant cytoplasm and a large euchromatic nucleus. Mitoses varied in frequency.

Large subcapsular colonies were also present in the spleen of the inoculated mice. In contrast to the small colonies of blastoid cells, the large subcapsular colonies were more heterogeneous, with mitotic cells, and with pyknotic cells. Pyknosis is usually indicative of cell degeneration. The colonies were partially demarcated by endothelial/connective tissue, and were well vascularized with arterioles or venules. Occasionally, coagulation-necrosis was present centrally in the colonies. Although the larger colonies bore some resemblance to lymph node parenchyma (the paracortical region), the colonies are best characterized as undifferentiated.

The spleens of some inoculated animals contained assemblances of two or more megakaryocytes. The locale of these colonies was apparently unrelated to that of the "undifferentiated" colonies.

Example 11

Tumorigenicity of the NA Bone Marrow Cells

The NA bone marrow cells appear to regulate their own replication by the production of soluble factors, i.e., by autocrine self-proliferation. This method of replication, if deregulated, has been implicated as the primary step in tumor production and metastases (Lang et al., 1985). In order to determine if NA bone marrow cells were tumorigenic, athymic nude mice were inoculated intraperitoneally and subcutaneously with cells from B.BM.3, or HU.BM.2, or MU.BM.2. All three cell lines produced tumors; tumor production was independent of the route of inoculation. Tumor cells were recovered from both the solid tumors and from the peritoneum, and were successfully recultured in vitro.

As a control, the cell lines B.BM.3 and HU.BM.2 were screened for retroviruses using both electron microscopy and an assay for reverse transcriptase.

The procedure for determining reverse transcriptase activity was the following. The supernatant fluid from the bone marrow cell lines were subjected to ultracentrifugation in order to capture any potential retroviruses in the resulting pellet. The pellet was reconstituted into a small volume of buffer (RT buffer) prior to analysis, which was performed according to the procedure described in Wu et al. (1973) Proc. Nat'l Acad. Sci. USA 70:1289-1302.

The results of both the analysis by electron microscopy, and by the assay for reverse transcriptase indicated that the cells were negative for infection by retroviruses.

Example 12

The Role of Soluble Factors Present In Conditioned Medium: Stimulation of The Appearance and Proliferation Of NA Bone Marrow Cells Conditioned medium was obtained by passing the supernatant from B.BM.1 cultures after the cultures had reached confluency, through a 0.22 micron filter. The conditioned medium was added to bone marrow stromal cultures from another calf; the bone marrow stromal cultures were prepared as discussed in Example 1. NA cells were observed in these cultures four to six days after treatment. In the absence of conditioned medium, it usually requires approximately two months for NA cells to arise. The NA cell line derived from the bovine bone marrow stromal culture treated with conditioned medium has been named B.BM.3.

Example 13

Figure 4:
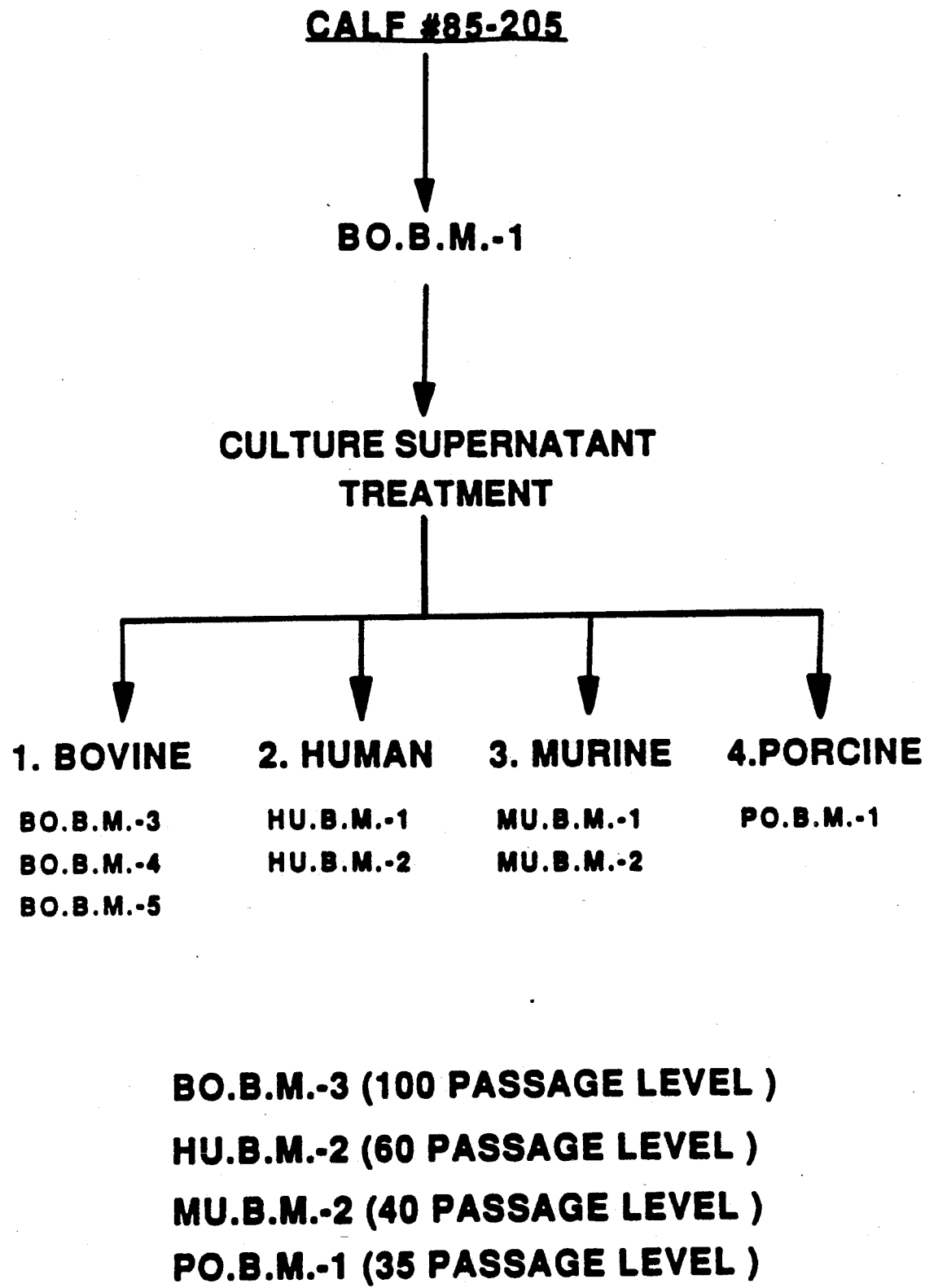
FIG. 4 is a chart showing the derivation of NA cell lines.

The Role of Soluble Factors Present In Conditioned Medium: Stimulation of The Appearance and Proliferation of Heterologous NA Bone Marrow Cells In order to determine whether the factor(s) in conditioned medium from bovine stromal cell cultures would be active in stimulating the appearance and proliferation of NA bone marrow cells from other species, bone marrow stromal cultures from mouse, human pig, and turkey were treated with conditioned medium. In all cases, the conditioned medium caused a decrease in the time required for the appearance of NA cells. The NA cell lines derived from this treatment are shown in FIG. 4.

Example 14

Production of Primitive Cell Colony Stimulating Factor (PC-CSF)

Conditioned medium from stromal cells, which contains the PC-CSF which induces normal bone marrow stromal cultures to produce a primitive NA bone marrow cell with potential pluripotent function, is prepared as follows.

The B.BM.3 parent cell culture (in 75 cm$^2$ flasks) was cultured at 37° C. in a gassed (5% CO$_2$ in air) humidified incubator until the stromal cell (adherent) reached confluency. Excess NA cells were removed daily during this period of culture. Once the Stroma reached confluency, the culture medium was removed and fresh media added to the culture. The culture was then reincubated for a further 24-30 hours. After incubation the supernatant was harvested, centrifuged (2000 RPM for 10 minutes) and filtered using a 0.22 micron millipore filter. The filtrate is stored at −70° C.

Example 15

Assay for PC-CSF Activity

Cultures of bovine stromal cultures in 100 mm diameter petri dishes which had grown to confluency, prepared as described below, were washed free of culture media, and crude PC-CSF, prepared as in Example 14, was added. The added PC-CSF was undiluted, or was in various two-fold dilutions ranging from ½ to 1/256. The plates were incubated for 4 hours at 37° C. in a gassed humidified incubator. After the initial incubation, 10 ml of growth medium (antibiotic free-RPMI-1640 supplemented with 10% fetal bovine serum) was added, and the plates were further incubated for a minimum of 14 days. The PC-CSF treated cultures were examined daily for the appearance of colonies of NA cells, and the results recorded.

In order to prepare bovine bone marrow stromal cell cultures, citrated bone marrow samples were collected from either the iliac crest or sternum of anesthetized calves, which were less than 1 year old. The bone marrow aspirates were centrifuged at room temperature at 2000 RPM for 15 minutes. The supernatant was removed, and the resulting cell pellet was resuspended in Minimal Essential Medium (MEM) supplemented with antibiotics. The cell suspension was layered onto a ficoll-hypaque density gradient and centrifuged for 30 minutes at 2000 RPM at room temperature. After centrifugation, the cells at the interface of the gradient were collected, and washed by dilution in MEM, followed by centrifugation at 1000 RPM for 8 minutes. This washing was repeated four times. Following the final wash, the cells were resuspended in antibiotic-free RPMI-1640 containing 10% fetal bovine serum, counted, and diluted to a final concentration of 5 ×10$^6$ cells per ml. The cell suspension was plated into a sterile, tissue culture prepared, 100 mm diameter petri dish, at a cell concentration of 5×10$^6$ cells/plate in 15 ml of growth medium, and incubated at 37° C. in a gassed (5% CO$_2$ in air) humidified incubator. The cultures were examined daily for the appearance of adherent stromal cell colonies, which routinely appeared after from 7 to 12 days of culture. When the stromal colonies appeared, the cultures were washed free of NA cells, and the growth media replenished. Upon reaching confluency, the stromal cell cultures were dispersed by treatment with trypsin-EDTA, and the resulting cell suspensions were further passaged into new 100 mm diameter petri dishes. The stromal cultures were routinely passaged once a week. Aliquots of the passaged cells were stored in liquid nitrogen in a storage medium consisting of RPMI-1640 supplemented with 10% fetal bovine serum and 10% DMSO.

The results of a crude PC-CSF assay are presented in FIG. 5. Colonies of NA cells appeared 4-7 days after treatment with undiluted PC-CSF containing conditioned medium. In FIG. 5, the plus symbols represent the number of colonies detected at day 14. In the absence of PC-CSF containing conditioned medium, NA colonies were not detected at this time. Moreover, PC-CSF activity was detectable at a 1/16 dilution of the conditioned medium.

Example 16

Clonogenic Assay for PC-CSF

The activity of PC-CSF was determined using a clonogenic assay according to the following method, which utilized sterile techniques, glassware, and media. Conditioned medium containing putative PC-CSF was diluted in $\log_{10}$ dilutions ($10^0$–$10^4$). An 0.5 ml aliquot containing $1 \times 10^6$ bone marrow cells was mixed with 0.5 ml of appropriately diluted conditioned medium, in a 5 ml vial. The bone marrow cells were prepared as described below. Into each of these vials was then added 1.0 ml of methyl cellulose (1.6%) in RPMI-1640. The vials were mixed, and 1.0 ml of the mixture was added to a Costar 35 × 10 mm petri dish. Each assay was carried out in duplicate. The plates were gently tipped back and forth and side-to-side to distribute medium evenly over the surface of the dish. The petri dishes were then placed into 150 mm diameter petri dishes, each of which had an uncovered 35 × 10 mm petri dish containing water to maintain humidity. The large petri dishes were then placed at 37° C. in an atmosphere of 5% $CO_2$ in air. The plates were examined daily for 10 days, and colonies were counted using an inverted microscope.

The bone marrow cell suspension for use in the clonogenic assay was obtained from a bone marrow aspirate collected in 2x-citrate from the iliac crest of an anesthetized calf (less than 1 year old). The bone marrow sample was washed free of citrate using MEM, and centrifuged at room temperature at 2000 RPM for 15 minutes. The cell pellet was resuspended in MEM and the cell suspension layered onto a ficoll-hypaque density gradient, and centrifuged at 2000 RPM for 30 minutes at room temperature. Following centrifugation the cells at the interface of the gradient were collected, diluted in MEM and centrifuged at 1000 RPM for 8 minutes at room temperature. Washing was repeated twice, and then the cells were resuspended in RPMI-1640 supplemented with 10% fetal bovine serum. The cell suspension was adjusted to yield a final cell concentration of $2 \times 10^6$ cells/ml.

The results obtained from the clonogenic assay were as follows. During the daily examination of the plates, colonies of less than 10 cells were observed by three days post culture, and of greater than 15 cells per colony were present at four days of culture. To titrate and obtain a final concentration of PC-CSF activity, it is preferable to incubate the cultures for 10 days.

Morphologically, the cells in the resultant colonies appeared to be similar to the NA cell lines from which the conditioned medium was generated. No other type(s) of cell colonies were observed. One further observation was that while the supernatant from the NA cell exhibited PC-CSF activity, this activity was enhanced significantly by incubating the NA cells with bovine bone marrow stromal cultures. Moreover, it seems that this enhancement of activity occurred even when the NA cell was heterologous to the bone marrow stroma, i.e., BO.BM.3 (NA cells) incubated with stroma isolated from BO.BM.001.

The clonogenic assay appears to be significantly more sensitive than the technique which measures the induction of stromal cells. Maximal PC-CSF activity was achieved at a 1/16 dilution of the supernatant using the induction of stromal cells, while peak activity for the same supernatant in the clonogenic assay was achieved with a dilution in the range of 1/100 to 1/1000.

It was also noted that, at the concentrations giving peak PC-CSF activity in the clonogenic assay, clones of stromal cells were also seen to be proliferating. Normally, clones of stromal cells do not appear before 10–14 days in culture. Therefore, the culture supernatant also appears to enhance the proliferation of stromal cells present in bone marrow cultures.

Example 17

Purification of PC-CSF-alpha and PC-CSF-beta

Figure 6:
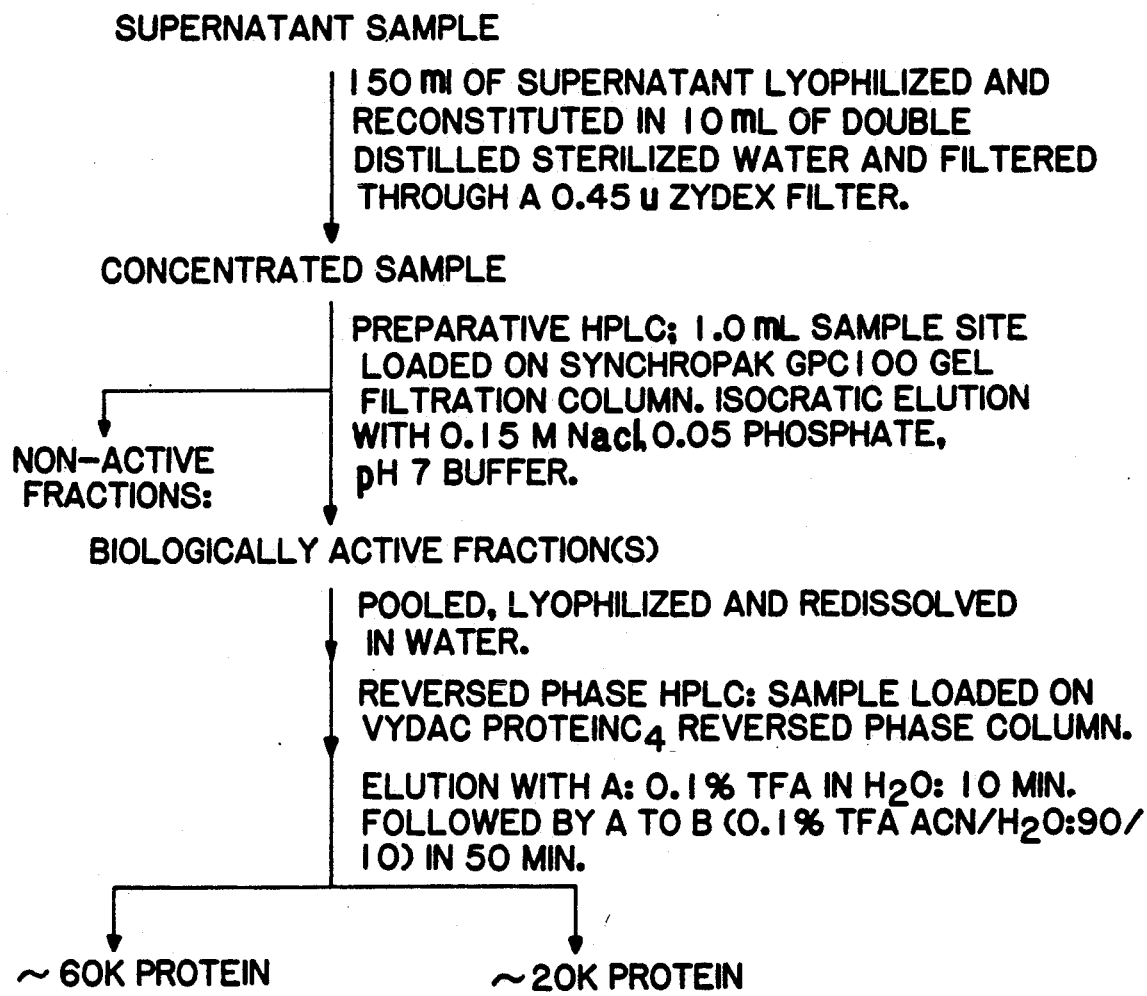
FIG. 6 is a chart showing a purification scheme for PC-CSF.

PC-CSF-alpha and PC-CSF-beta were purified from conditioned medium derived from murine stromal cell cultures and murine NA cell cultures according to Scheme A, shown in FIG. 6.

According to the scheme, conditioned medium is obtained essentially as described in Example 12, supra, except that the medium is from the appropriate stromal and/or NA cell cultures. Approximately 20 ml of the conditioned medium is concentrated to approximately 1800 microliters. Alternatively, to concentrate the sample, the medium is lyophilized, and the dried material is redissolved in sterilized doubly distilled water to give a sample which is approximately 15 times concentrated. The concentrated sample is filtered through a 0.45 micron Zydex filter, and is subjected to HPLC gel filtration on a column of Synchropak GPC 100 (Synchrom Inc., Lafayette, Ind., U.S.A.); the column dimensions are 500 mm × 10 mm (inner diameter). Proteins are eluted from the column by an isocratic elution with buffer containing 0.15M NaCl, 0.05 M phosphate, pH 7.0. In order to determine which eluted fractions contain PC-CSF, the biological activity of the fractions is determined using the clonogenic assay described supra. The desired fractions, which contain PC-CSF activity, are pooled, lyophilized, and dissolved in sterile double distilled water. The solution containing PC-CSFs is then subjected to preparative reverse phase high performance liquid chromatography using a Varian LC 5500 The sample is loaded onto a Vydac Protein $C_4$ reversed phase column (Vydac Separation Group, California, USA), and the PC-CSFs eluted. Elution is with solution A (0.1% trifluoracetic acid in water) for 10 minutes, followed by A to B (0.1% trifluoracetic acid, acetonitrile in water (90:10) in 50 minutes. This chromatography yields two major components with PC-CSF activity; i.e., PC-CSF-alpha which has an apparent molecular weight of approximately 20 Kd, and PC-CSF-beta which has an apparent molecular weight of approximately 60–70 Kd.

Isolated fractions were analyzed by HPLC on a Vydac Protein $C_4$ reversed phase analytical column (150 × 4.5 mm I.D.) and by fast protein liquid chromatography (FPLC).

Based upon the chromatographic patterns of the fractions containing PC-CSF activity, it is estimated that PC-CSF-alpha has been purified to apparent homogeneity, and that PC-CSF-beta is approximately 70–80% pure. The HPLC Reversed phase profile of the PC-CSF-beta fraction is suggestive of a contamination with a low concentration of PC-CSF-alpha.

Both PC-CSF-alpha and PC-CSF-beta have been tested for their ability to induce Primitive Cell-Colony Forming Units (PC-CFU) in the clonogenic assay, described supra. Both PC-CSFs are able to induce PC-CFUs. Also, it appears that the activity of PC-CSFbeta, when combined with PC-CSF-alpha, is at least additive, and may be synergistic.

Example 18

Identification of the Source Cells of PC-CSF-alpha and PC-CSF-beta

The conditioned media obtained from cultures of stromal cells alone, NA cells alone, and a combination of stromal cells and NA cells were analyzed by vertical polyacrylamide gel electrophoresis in the presence of SDS. The gel patterns showed that a protein with a comparable molecular weight to that of PC-CSF-alpha (i.e., 20-25 Kd) is present in the conditioned media from NA cells, and from stromal cells plus NA cells. A protein with a comparable molecular weight to that of PC-CSF-beta (i.e., 60-70 Kd) is present in the conditioned media from stromal cells, and from stromal cells plus NA cells. This data is suggestive that the 20-25 Kd protein is a product of the NA cells, while the 60-70 Kd protein is a product of the stromal cells.

Deposit Information

The following cell lines have been deposited under the terms of the Budapest Treaty with the American Type Culture Collection (ATCC), 12301 Parklawn Dr., Rockville, Md. 20852, and have been assigned the following Accession Numbers.

| Cell line | ATCC No. | Deposit Date |
|---|---|---|
| BoBm3 + 80 | CRL-9825 | Sept. 14, 1988 |
| MoBm2 + 44 | CRL-9826 | Sept. 14, 1988 |
| BoBm Stroma + | CRL-9827 | Sept. 14, 1988 |
| PoBm2 + 12 | CRL-9828 | Sept. 14, 1988 |
| HwBm2 + 40 | CRL-9829 | Sept. 14, 1988 |

Upon allowance and issuance of this application as a United States Patent, all restriction on availability of these deposits will be irrevocably removed; and access to the designated deposits will be available during pendency of the above-named application to one determined by the Commissioner to be entitled thereto under 37 CFR 1.14 and 35 USC 1.22. Moreover, the designated deposits will be maintained for a period of thirty (30) years from the date of deposit, or for five (5) years after the last request for the deposit; or for the enforceable life of the U.S. patent, whichever is longer. These deposits are intended for convenience only, and are not required to practice the present invention in view of the description here.

References

The following references have been cited in the discussion of the invention.

Barr et al. (1986) Biotechniques 4:428.
Barlozzaci et al. (1987) Proc. Nat'l Acad. Sci. USA 84:7691.
Biofeldt Ohmann (1987) J. Histochem. Cytochem. 35:627.
Botstein (1979) Gene 8:17.
Broach (1981) Molecular Biology of the Yeast Saccharomyces 1:445 (Cold Spring Harbor Press).
Broach et al. (1983) Meth. Enz. 101:307.
Chang et al. (1977) Nature 198:1056.
Clewell et al. (1969) Proc. Nat'l Acad. Sci. USA 62:1159.
Clewell (1972) J. Bacteriol. 110:667.
Cohen (1972) Proc. Nat'l Acad. Sci. USA 69:2110.
De Boer et al. (1983) Proc. Nat'l Acad. Sci. USA 292:128.
Fiers et al. (1978) Nature 273:113.
Goeddel et al. (1980) Nucleic Acids Res. 8:4057.
Graham and Van der Eb (1978) Virology 52:546.
Grunstein and Hogness (1975) Proc. Nat'l Acad. Sci. USA 73:3961.
Hammerling et al. (1981) Monoclonal Antibodies and T-Cell Hybridomas.
Hess et al. (1968) J. Adv. Enzyme Reg. 7:149.
Hinnen et al. (1978) Proc. Nat'l Acad. Sci. 75:1929.
Hitzeman et al. (1980) J. Biol. Chem. 255:2073.
Holland et al. (1978) Biochemistry 17:4900.
Holland (1981) J. Biol. Chem. 256: 1385.
Kennett et al. (1980) Monoclonal Antibodies.
Laemmli (1970) Nature 227:680.
Lang et al. (1985) Cell 43:531.
Maniatis et al. (1982) Molecular Cloning: A Laboratory Manual (Cold Spring Harbor Press, Cold Spring Harbor, N.Y.).
Mayer and Walker eds. (1987) Immunochemical Methods in Cell and Molecular Biology (Academic Press, London).
Maxam et al. (1980) Methods in Enzymology 65:499.
Sanger et al. (1977) Proc. Nat'l Acad. Sci. USA 74:5463.
Schreier et al. (1980) Hybridoma Techniques.
Scopes (1987) Protein Purification, 2nd ed. (Springer Verlag).
Shimatake et al. (1981) Nature 292:128.
Warner (1984) DNA 3:401.
Wu and Grossman (1987) Methods in Enzymology Vol. 154, Recombinant DNA, Part E.
Wu (1987) Methods in Enzymology Vol. 155, Recombinant DNA, Part F.
Zoller (1982) Nucleic Acids Res. 10:6487.

Industrial Applicability

The NA cells of the invention have commercial utility for the production of PC-CSF, and for cell replacement therapy in individuals requiring such therapy as a result of hematopoietic disorders. The monoclonal antibodies to NA cells are useful for the isolation and identification of these NA cells.

PC-CSFs may be useful in therapy for hematopoietic disorders. In particular, if they alter significantly the rate of hematopoiesis, they may also have potential in regulating early immunity, particularly in reference to neonates and their immune response to infectious diseases. The latter is of import not only to humans, but also in the treatment of domestic animals, including agricultural animals. In addition, PC-CSFs may also have use in augmenting bone marrow transplantation therapy, since they are stimulatory agents for NA cells.

In addition to the above, PC-CSFs may also have use in other cases where cell proliferation is desired, for example, in wound healing, and in the stimulation of the growth of nerve cells, particularly those which have become senile.

We claim:

1. A suspension of mammalian, non-murine, non-human cells comprised of pluripotent lymphohematopoietic non-adherent progenitor stem cells (NA cells) substantially free of mature lymphoid and myeloid cells wherein said NA cells
    (a) are capable of producing PC-CSF;

(b) substantially lack T cell specific antigens, MHC class II antigens, macrophage/monocyte markers and B cell markers; and
(c) are not induced to differentiate in vitro into cells of the lymphoid or myeloid series with gamma-interferon, alpha-interferon, alpha-tumor necrosis factor, or interleukin 2.

2. A suspension of pluripotent lymphohematopoietic non-adherent progenitor stem cells (NA cells) derived from a human, wherein said NA cells
(a) are not immunologically reactive with a monoclonal antibody directed against My10 antigen, said monoclonal antibody being produced by hybridoma cell line ATCC Accession No. HB-8483;
(b) are capable of producing PC-CSF;
(c) substantially lack T cell specific antigens, MHC class II antigens, macrophage/monocyte markers and B cell markers; and
(d) are not induced to differentiate in vitro into cells of the lymphoid or myeloid series with gamma-interferon, alpha-interferon, alpha-tumor necrosis factor, or interleukin 2.

3. A method of producing a suspension of cells according to claim 9, which method comprises:
(a) providing a cell suspension of mammalian, non-murine, non-human bone marrow cells;
(b) growing said cell suspension of step a in a culture medium comprised of components essential to cell growth and under conditions which promote cell growth;
(c) isolating and recovering a population of NA cells from the cell culture resulting from step b; and
(d) growing the isolated suspension of cells from step c in a culture medium comprised of components essential to cell growth and under conditions which promote cell growth to yield a suspension of NA cells.

4. A suspension of cells according to claim 1, wherein the cells are bovine cells.

5. The method of claim 3 in which the cells are bovine.

6. A method of producing a suspension of cells according to claim 2, which method comprises:
(a) providing a cell suspension comprising human bone marrow cells;
(b) growing said cell suspension from step a in a culture medium comprised of components essential to cell growth and under conditions which promote cell growth;
(c) isolating and recovering a population of NA cells from the cell culture resulting from step b; and
(d) growing the isolated suspension of cells from step c in a culture method comprised of components essential to cell growth and under conditions which promote cell growth to yield a suspension of NA cells.

7. The method of claim 3 wherein PC-CSF is added to the culture medium during step b.

8. The method of claim 6 wherein PC-CSF is added to the culture medium during step b.

* * * * *